United States Patent
Johnson

(10) Patent No.: US 10,058,135 B1
(45) Date of Patent: *Aug. 28, 2018

(54) SENSITIVITY ENHANCEMENT GLOVE

(71) Applicant: Lanny L. Johnson, Frankfort, MI (US)

(72) Inventor: Lanny L. Johnson, Frankfort, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,988

(22) Filed: Jan. 29, 2018

Related U.S. Application Data

(63) Continuation of application No. 15/801,440, filed on Nov. 2, 2017, now Pat. No. 9,918,504.

(51) Int. Cl.
*A41D 19/00* (2006.01)

(52) U.S. Cl.
CPC ..... *A41D 19/0013* (2013.01); *A41D 19/0017* (2013.01)

(58) Field of Classification Search
CPC .......... A41D 19/0013; A41D 19/0017
See application file for complete search history.

(56) References Cited

U.S. PATENT DOCUMENTS

| | | |
|---|---|---|
| 1,679,836 A | 8/1928 | Linder |
| 2,118,463 A | 5/1938 | Eden |
| 2,253,710 A | 8/1941 | Jones et al. |
| 4,195,365 A | 4/1980 | Eyman et al. |
| 4,416,026 A | 11/1983 | Smith |
| 4,654,895 A | 4/1987 | Peters |
| 4,712,253 A | 12/1987 | Chen |
| 5,829,061 A | 11/1998 | Visgil et al. |
| D403,138 S | 12/1998 | Wilmot |
| 7,159,246 B2 | 1/2007 | Tippey |
| 7,487,553 B2 | 2/2009 | Price |
| 8,448,265 B2 | 5/2013 | DuPont |
| D713,122 S | 9/2014 | Barbee |
| D747,071 S | 1/2016 | Jung |
| 9,642,406 B2 | 5/2017 | Kusjanovic |
| 2004/0064870 A1 | 4/2004 | Gold |
| 2008/0010718 A1 | 1/2008 | Richards |
| 2013/0074241 A1 | 3/2013 | Gellis |

OTHER PUBLICATIONS

Zhao et al; "Neural network models of the tactile system develop first-order units with spatially complex receptive fields"; preprint first posted online Jul. 17, 2017; doi: http://dx.doi.org/10.1101/164954.

*Primary Examiner* — Khaled Annis

(74) *Attorney, Agent, or Firm* — Dawsey Co., LPA; David J. Dawsey

(57) ABSTRACT

A sensitivity enhancement glove having at least one sleeve with a unique aperture to enhance performance by capitalizing on neuroanatomy and create hyper sensitivity and thereby enhance effects on proprioception and simultaneous musculoskeletal functions.

20 Claims, 11 Drawing Sheets

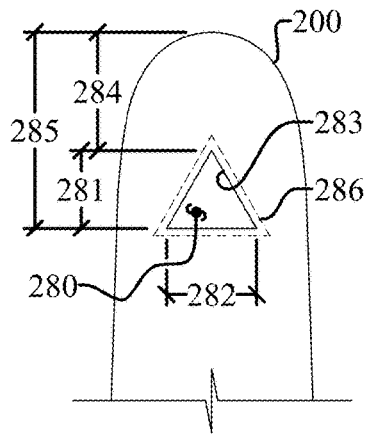
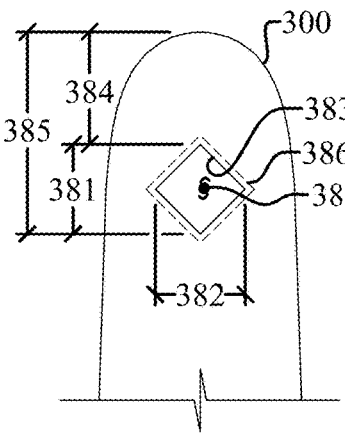
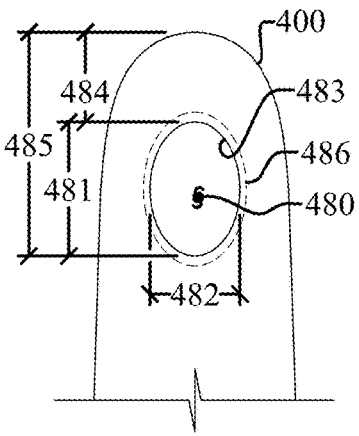
*Fig. 10*    *Fig. 11*    *Fig. 12*
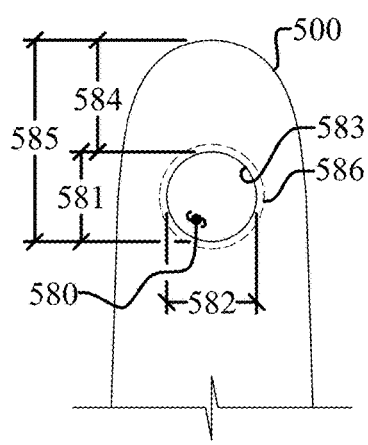
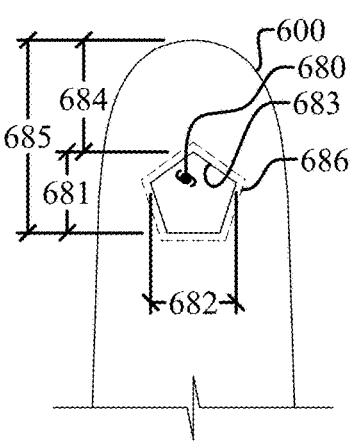
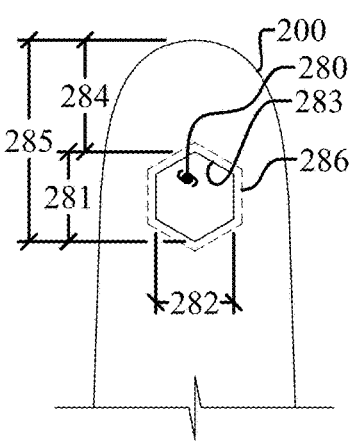
*Fig. 13*    *Fig. 14*    *Fig. 15*

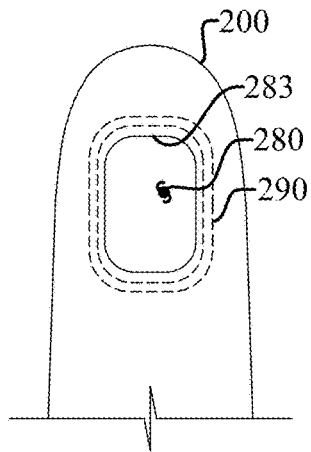
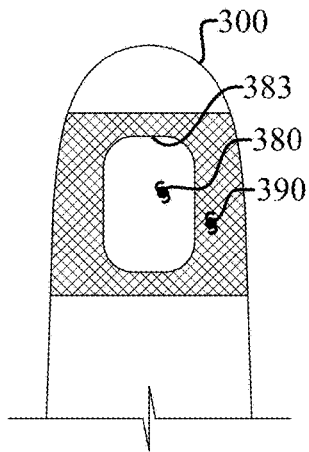
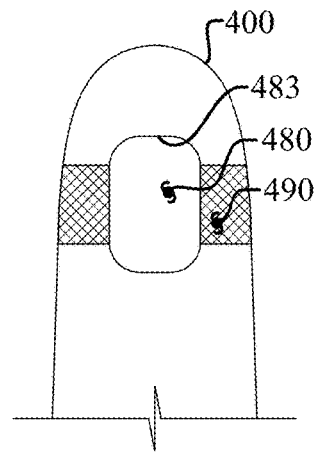
*Fig. 16*  *Fig. 17*  *Fig. 18*
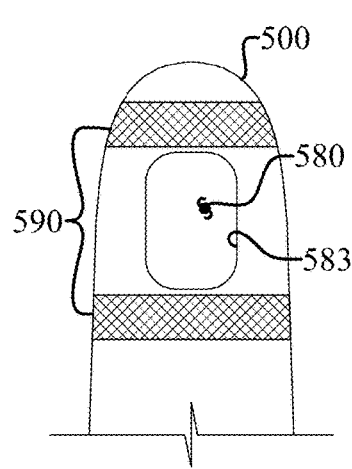
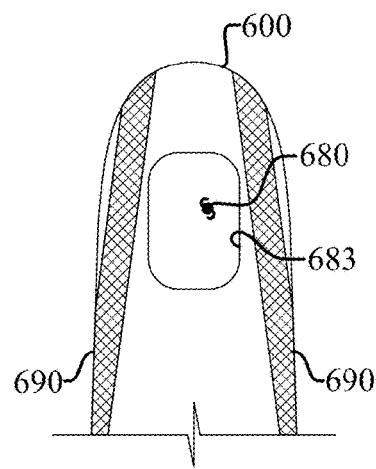
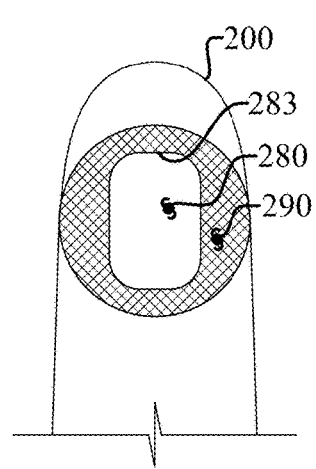
*Fig. 19*  *Fig. 20*  *Fig. 21*

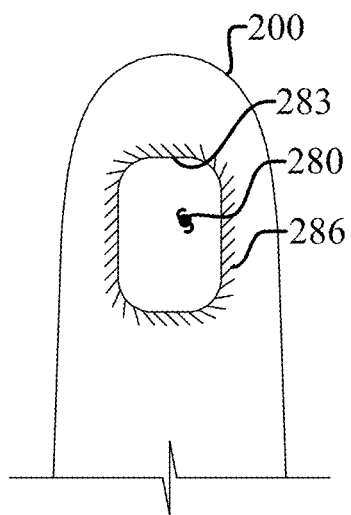
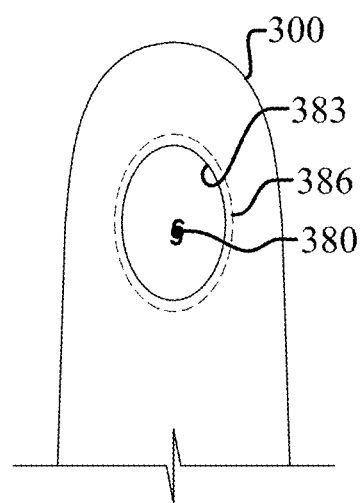
*Fig. 22*
*Fig. 23*
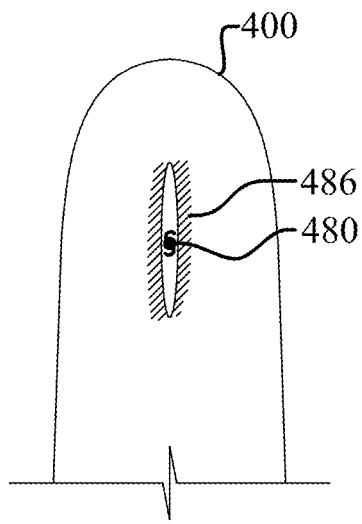
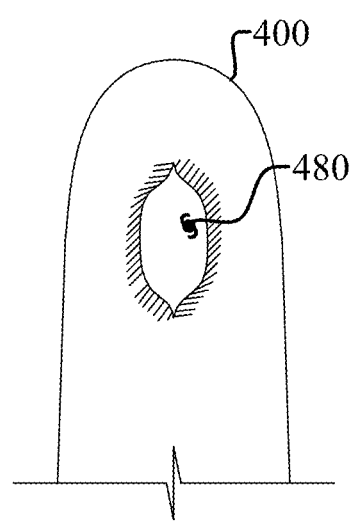
*Fig. 24*
*Fig. 25*

US 10,058,135 B1

SENSITIVITY ENHANCEMENT GLOVE

CROSS-REFERENCE TO RELATED APPLICATIONS

This application is a continuation application of U.S. patent application Ser. No. 15/801,440, filed on Nov. 2, 2017.

TECHNICAL FIELD

The present disclosure relates to the field of gloves, digit sleeves, garments, and wearables, and more particularly, to such devices, and associated methods and systems, that enhance sensitivity of select areas of the human body.

BACKGROUND OF THE INVENTION

In the past little has been done in the field of gloves and finger sleeves, as well as wearables, to capitalize on the extraordinary senses of the human body and harness the associated performance benefits. The present invention is directed to improving tactile sensation, and in some embodiments capitalizing on neuroanatomy to create hyper sensitivity and thereby enhance effects on proprioception and simultaneous musculoskeletal functions

SUMMARY OF INVENTION

In its most general configuration, the presently disclosed glove, finger/thumb sleeve(s), wearables, systems, and methods advance the state of the art with a variety of new capabilities and overcome many of the shortcomings of prior devices in new and novel ways. The presently disclosed glove, finger/thumb sleeve(s), wearables, systems, and methods overcome the shortcomings and limitations of the prior art in any of a number of generally effective configurations. The presently disclosed glove, finger/thumb sleeve(s), wearables, systems, and methods demonstrate such capabilities and overcome many of the shortcomings of prior methods in new and novel ways of improving tactile sensation, and in some embodiments capitalize on neuroanatomy to create hyper sensitivity and thereby enhance effects on proprioception and simultaneous musculoskeletal functions.

BRIEF DESCRIPTION OF THE DRAWINGS

Without limiting the scope of the sports equipment handle and system as claimed below and referring now to the drawings and figures:

FIG. 10 is a bottom plan view of an embodiment of a glove finger portion, not to scale;

FIG. 11 is a bottom plan view of an embodiment of a glove finger portion, not to scale;

FIG. 12 is a bottom plan view of an embodiment of a glove finger portion, not to scale;

FIG. 13 is a bottom plan view of an embodiment of a glove finger portion, not to scale;

FIG. 14 is a bottom plan view of an embodiment of a glove finger portion, not to scale;

FIG. 15 is a bottom plan view of an embodiment of a glove finger portion, not to scale;

FIG. 16 is a bottom plan view of an embodiment of a glove finger portion, not to scale;

FIG. 17 is a bottom plan view of an embodiment of a glove finger portion, not to scale;

FIG. 18 is a bottom plan view of an embodiment of a glove finger portion, not to scale;

FIG. 19 is a bottom plan view of an embodiment of a glove finger portion, not to scale;

FIG. 20 is a bottom plan view of an embodiment of a glove finger portion, not to scale;

FIG. 21 is a bottom plan view of an embodiment of a glove finger portion, not to scale;

FIG. 22 is a bottom plan view of an embodiment of a glove finger portion, not to scale;

FIG. 23 is a bottom plan view of an embodiment of a glove finger portion, not to scale;

FIG. 24 is a bottom plan view of an embodiment of a glove finger portion, not to scale;

FIG. 25 is a bottom plan view of an embodiment of a glove finger portion, not to scale;

Figure 1:
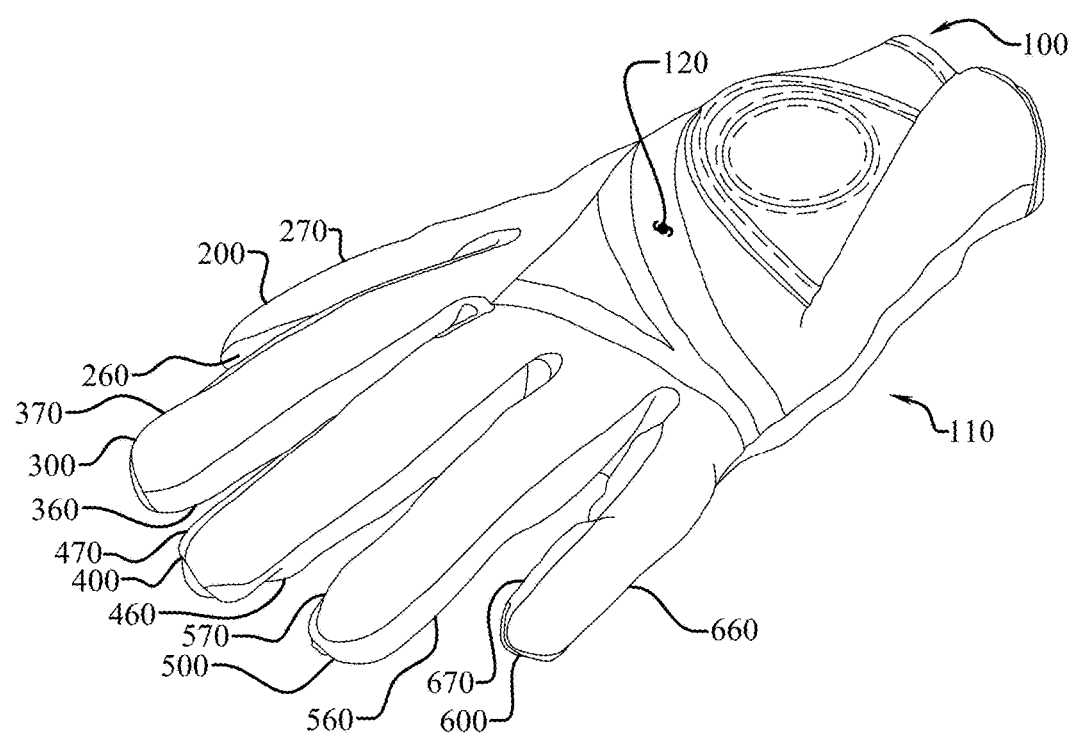
FIG. 1 is an isometric view of an embodiment of a glove, not to scale.

These drawings are provided to assist in the understanding of the exemplary embodiments of the presently disclosed gloves and finger/thumb sleeves, as described in more detail below and should not be construed as unduly limiting the gloves and sleeves. In particular, the relative spacing, positioning, sizing and dimensions of the various elements illustrated in the drawings are not drawn to scale and may have been exaggerated, reduced or otherwise modified for the purpose of improved clarity. Those of ordinary skill in the art will also appreciate that a range of alternative configurations have been omitted simply to improve the clarity and reduce the number of drawings.

DETAILED DESCRIPTION OF THE INVENTION

A glove, finger/thumb sleeve(s), system, and method designed to provide improved tactile sensation, and in some embodiments capitalize on neuroanatomy to create hyper sensitivity and thereby enhance effects on proprioception and simultaneous musculoskeletal functions. Research has shown that the glove, finger/thumb sleeve(s), system, and method, increase relative sensitivity between the covered portion of the hand and/or digits and the uncovered, or exposed, areas, particularly areas overlying the volar aspect of one or more of the distal phalange of finger and/or the thumb, as well as other embodiments having exposed areas of the palm and/or dorsum side of the hand. The glove, sleeve(s), system, and method produce an increase in neurosensory input that results in enhanced proprioception of the same extremity, which automatically provides a user improved psychomotor performance in various tasks or sports, as will be explained throughout, and running the gamut from typing to reading braille, gripping a golf grip to throwing a football or shooting a basketball, video gaming to machine operation via contact with a wheel, knob, stick, remote control instrumentation, and/or joy stick, just to name a few. A variety of unique and nonobvious variables, and relationships among the variables, disclosed herein influence the improved sensitivity in the uncovered areas, as well as the difference in sensitivity between covered and uncovered areas and provide a user with enhanced tactile biofeedback enabling a significant advance in the state of the art. The preferred embodiments of the device accomplish this by new and novel arrangements of elements and methods that are configured in unique and novel ways and which demonstrate previously unavailable but preferred and desirable capabilities. The detailed description set forth below in connection with the drawings is intended merely as a description of the presently preferred embodiments, and is not intended to represent the only form, systems, and methods which may be constructed or utilized. The description sets forth the designs, functions, means, and methods in connection with the illustrated embodiments. It is to be understood, however, that the same or equivalent functions and features may be accomplished by different embodiments that are also intended to be encompassed within the spirit and scope.

Figure 2:
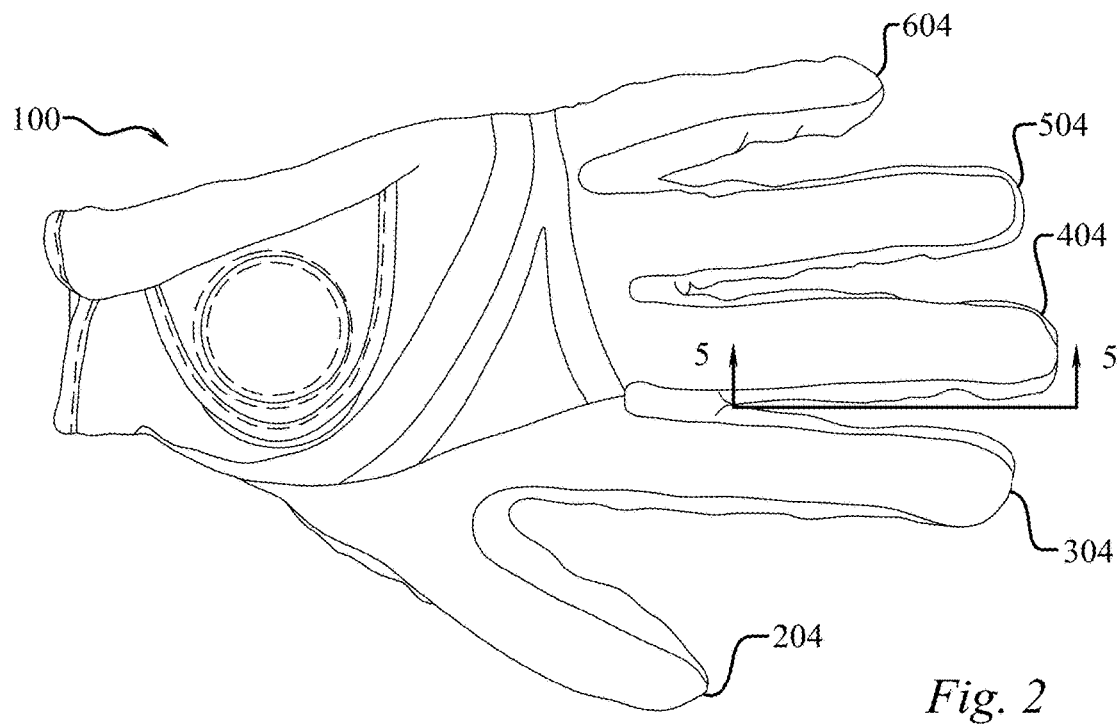
FIG. 2 is a top plan view of an embodiment of a glove, not to scale.
Figure 3:
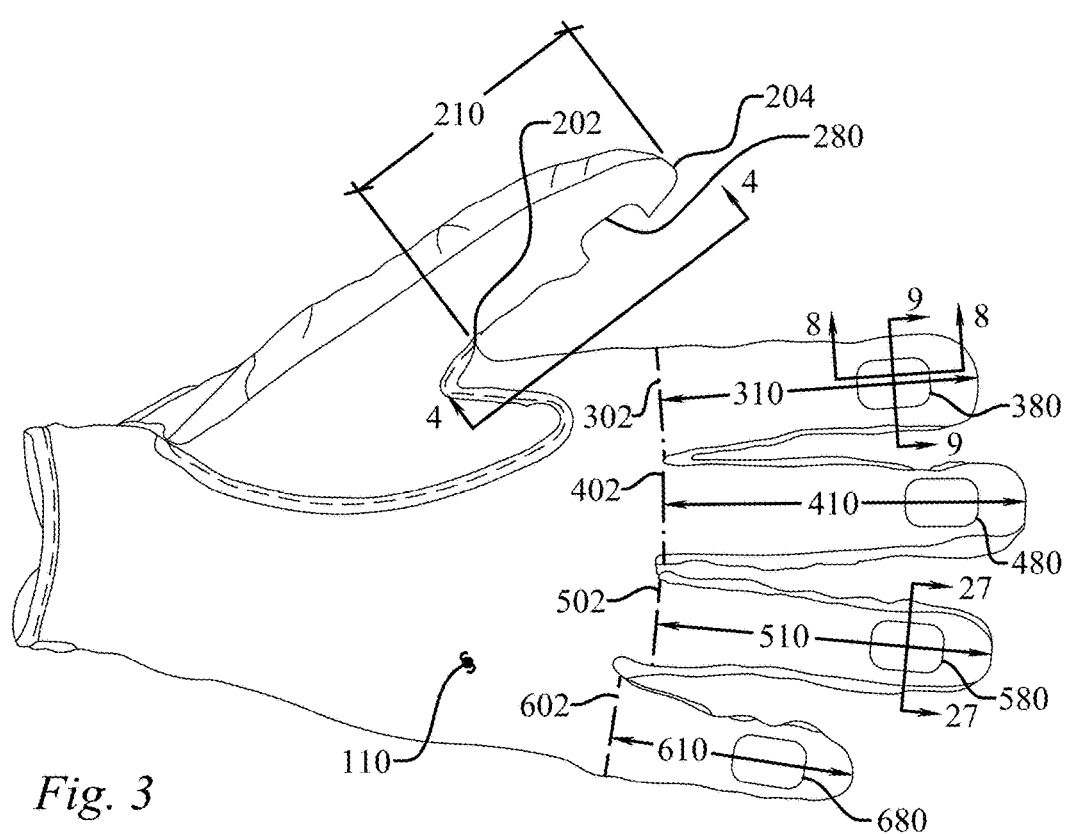
FIG. 3 is a bottom plan view of the embodiment an embodiment of a glove, not to scale.

As seen in FIGS. 1-3, the structure of the glove (100) may include a palm side (110) and a dorsum side (120). The glove (100) may include one or more of a thumb sleeve (200), index finger sleeve (300), middle finger sleeve (400), ring finger sleeve (500), and small finger sleeve (600); however the sleeves may also be separate and independent structures designed to be fitted on one or more fingers and/or thumb without the traditional body of a glove. Thus, all of the disclosure herein applies equally to glove embodiments having one to five attached, or attachable, sleeves, as well as individual sleeves that are applied to at least one finger or thumb and are not associated with a glove. As illustrated best in FIGS. 1, 2-7, 26, and 27, each sleeve, has a proximal end (X02), a distal end (X04), a sleeve length (X10), a sleeve depth (X20), a sleeve width (X30), a gripping surface (X40), a dorsum side surface (X50), a sinistral side surface (X60), a dextral side surface (X70), and an aperture (X80). To avoid excessive duplication of disclosure, one skilled in the art will appreciate that the values of "X" in the element numbers of the previous sentence are "2" when associated with a thumb sleeve (200), "3" when associated with an index finger sleeve (300), "4" when associated with a middle finger sleeve (400), "5" when associated with a ring finger sleeve (500), and "6" when associated with a small finger sleeve (600). Similarly, while FIGS. 5-7 specifically illustrate the middle finger sleeve (400), it also applies equally to the index finger sleeve (300), the ring finger sleeve (500), and the small finger sleeve (600), but with element numbers reflecting associated 300, 500, or 600 series, as illustrated for many elements in FIG. 26. Therefore, disclosure with respect to one sleeve applies equally to any of the sleeves.

Figure 4:
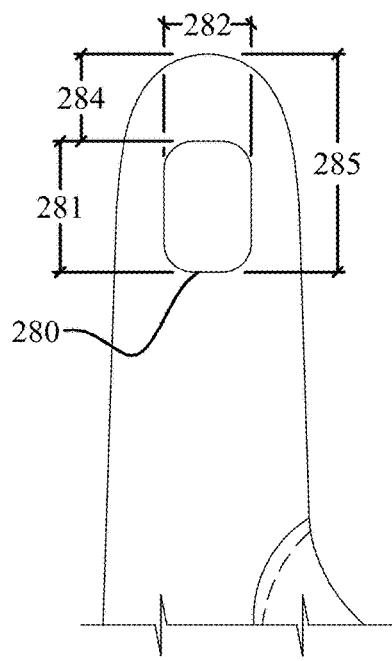
FIG. 4 is a sectional view of an embodiment of a glove thumb portion taken along section line 4-4 in FIG. 3, not to scale.
Figure 26:
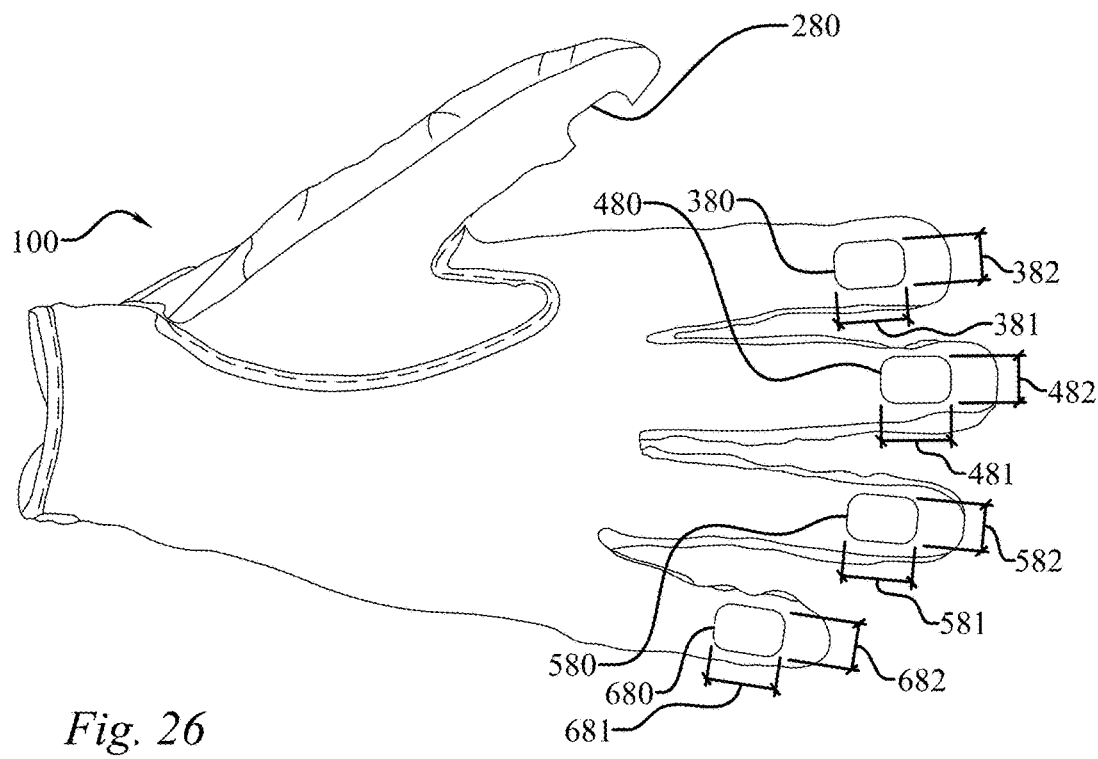
FIG. 26 is a bottom plan view of the embodiment an embodiment of a glove, not to scale.

As seen in FIG. 4, embodiments having a thumb sleeve (200) incorporate a thumb sleeve aperture (280) having a thumb sleeve aperture length (281), a thumb sleeve aperture width (282), a thumb sleeve aperture perimeter (283), a thumb sleeve aperture leading edge offset (284), a thumb sleeve trailing edge offset (285), and in some embodiments a thumb sleeve aperture reinforcement (286). Likewise, as seen in FIGS. 3, 11, and 26, embodiments having an index finger sleeve (300) incorporate an index finger sleeve aperture (380) having an index finger sleeve aperture length (381), an index finger sleeve aperture width (382), an index finger sleeve aperture perimeter (383), an index finger sleeve aperture leading edge offset (384), an index finger sleeve trailing edge offset (385), and in some embodiments an index finger sleeve aperture reinforcement (386). Similarly, as seen in FIGS. 3, 5-7, 12, and 26, embodiments having a middle finger sleeve (400) incorporate a middle finger sleeve aperture (480) having a middle finger sleeve aperture length (481), a middle finger sleeve aperture width (482), a middle finger sleeve aperture perimeter (483), a middle finger sleeve aperture leading edge offset (484), a middle finger sleeve trailing edge offset (485), and in some embodiments a middle finger sleeve aperture reinforcement (486). Likewise, as seen in FIGS. 3, 13, and 26, embodiments having a ring finger sleeve (500) incorporate a ring finger sleeve aperture (580) having a ring finger sleeve aperture length (581), a ring finger sleeve aperture width (582), a ring finger sleeve aperture perimeter (583), a ring finger sleeve aperture leading edge offset (584), a ring finger sleeve trailing edge offset (585), and in some embodiments a ring finger sleeve aperture reinforcement (586). Lastly, as seen in FIGS. 3, 14, and 26, embodiments having a small finger sleeve (600) incorporate a small finger sleeve aperture (680) having a small finger sleeve aperture length (681), a small finger sleeve aperture width (682), a small finger sleeve aperture perimeter (683), a small finger sleeve aperture leading edge offset (684), a small finger sleeve trailing edge offset (685), and in some embodiments a small finger sleeve aperture reinforcement (686).

The aperture reinforcement may include stitching along the aperture perimeter to provide additional durability and/or a raised perimeter edge, but may include the stitching, or joining, of an elastic reinforcement, or tacky non-slip reinforcement, around the perimeter to further achieve the goals expressed herein, as well as increasing the propensity of keeping the skin protruding through the aperture via a silicon, or elastomeric, reinforcement along the aperture perimeter. In some embodiments the reinforcement adds a desired degree of rigidity around the aperture to further increase the amount of tissue extending from the aperture. The palm side of the human hand has a durometer value ranging from approximately 25 to approximately 35 Shore A on the hardness scale. In one embodiment, the durometer of the reinforcement is at least 70 percent greater than the durometer value of the palm side of the human hand, which in a further embodiment has a durometer value greater than 60 Shore A on the hardness scale to ensure it is significantly harder than the adjacent portion of the hand, and in an even further embodiment it has a durometer value of at least 65 Shore A on the hardness scale. In one extreme embodiment the reinforcement is a metallic ring. In another embodiment the reinforcement has a degree of elasticity such that the aperture perimeter can extend at least 1 mm when subjected to the test glove procedure disclosed herein, and in a further embodiment it the aperture perimeter can extend at least 2 mm, and at least 3 mm in another embodiment. In another series of embodiments a upper limit is placed on the perimeter lengthening to no more than 10 mm in one embodiment, no more than 8 mm in another embodiment, and no more than 6 mm in still a further embodiment. This limited perimeter lengthening embodiments further serve to capture, or grasp, the skin standing proud of the aperture thereby enhancing sensitivity.

The skin of the dorsum of the hand is thin and pliable, it is attached to the hand's skeleton only by loose areolar tissue, where lymphatics and veins course. The skin of the palmar surface of the hand is unique, with characteristics for special function. The palmar skin is thick and glabrous and not as pliable as the dorsal skin. It is strongly attached to the underlying fascia by numerous vertical fibers. While these features enhance skin stability for proper grasping function, they also provide the opportunity to capitalize on the benefits of enhancing the sensitivity of this skin, after all the finger pads over the volar aspect of the distal phalanges of each digit are the most sensitive area of the fingers. The skin covering the volar aspect of the distal phalanges of the fingers and thumb have the most nerve endings and most specialized nerve ending called the pacinian corpuscle. The skin is most firmly anchored to the deep structures at the palmar creases; this is of clinical importance when planning surgical incisions, to minimize skin contractures. In contrast to the dorsal skin, the blood supply to the palmar skin is through numerous small, vertical branches from the common digital vessels. Therefore, the elevation of palmar skin flaps is limited. Finally, the skin of the palmar surface of the hand contains a high concentration of sensory nerve organs essential to the hand's normal function.

Figure 9:
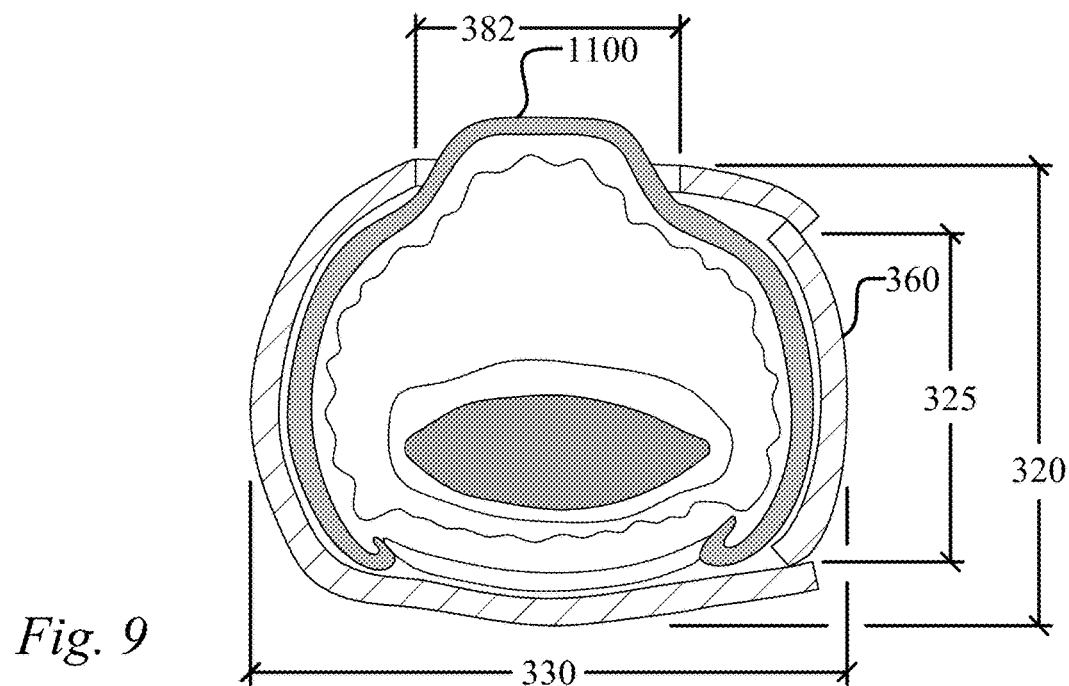
FIG. 9 is a cross-sectional view of an embodiment of a glove finger portion and finger taken along section line 9-9 in FIG. 3, not to scale.
Figure 27:
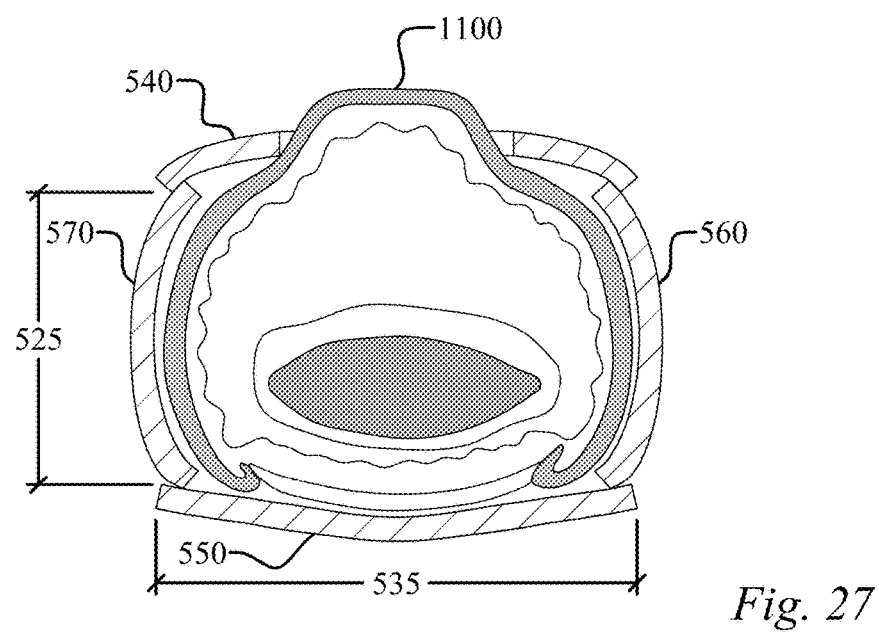
FIG. 27 is a cross-sectional view of an embodiment of a glove finger portion and finger, not to scale.

Each sleeve (200, 300, 400, 500, 600) may be constructed of a single tubular piece of material or an assembly of several panels joined together, often by sewing or adhesives, such as the index finger sleeve (300) of FIGS. 3 and 9 illustrating a distinct panel forming the index finger sinistral side surface (360), and the ring finger sleeve (500) of FIGS. 3 and 27 illustrating distinct panels forming the ring finder sinistral side surface (560), the ring finger dextral side surface (560), the ring finger gripping surface (540), as well as the ring finger dorsum side surface (550). In one embodiment the small finger sleeve (600) is constructed like the index finger sleeve (300) of FIG. 9 but mirrored so that the distinct side panel forms the dextral side surface (670), while in another embodiment the middle finger sleeve (400) is constructed like the ring finger sleeve (500) with a the middle finder sinistral side surface (460), the middle finger dextral side surface (470), the middle finger gripping surface (440), as well as the middle finger dorsum side surface (450), not illustrated but easily understood in light of FIGS. 9 and 27.

Each sleeve (200, 300, 400, 500, 600) has an associated sleeve depth, such as index finger sleeve depth (320) seen in FIG. 9, an associated sleeve width, such as the index finger sleeve width (330) also seen in FIG. 9, and an associated sleeve length (210, 310, 410, 510, 610), as seen in FIG. 3.

Thus, the thumb sleeve (200) has a thumb sleeve depth (220) and thumb sleeve width (230), the middle finger sleeve (400) has a middle finger sleeve depth (420) and middle finger sleeve width (430), the ring finger sleeve (500) has a ring finger sleeve depth (520) and ring finger sleeve width (530), and the small finger sleeve (600) has a small finger sleeve depth (620) and small finger sleeve width (630), as would be understood by one skilled in the art reflecting on FIG. 9. The sleeve depth, width, length, and circumference are measured using a test insert glove within the glove (100) and/or sleeves (200, 300, 400, 500, 600) and filled with high purity compressed nitrogen gas, 99.5-100%, CAS No: 7727-37-9, at 5 psig. The test glove is a sterile latex powdered surgical glove, such as Surgicare brand gloves by Kanam Latex Industries Pvt. Ltd. of Nagercoil, India, having a 280 mm length, 89 mm width, a finger thickness of 0.16 mm, a minimum tensile strength of 24 Mpa before ageing, a minimum ultimate elongation percentage of 750 before ageing, a maximum stress at 500% elongation of 5.5 Mpa, a minimum force at break of 9 N, and meeting international standards ASTM D 3577, EN 455 part I, II & III, and conforming to standards ASTM D 3578, EN 455 Part I & II. Thus, in embodiments of the glove (100) having four fingers sleeves (300, 400, 500, 600) and a thumb sleeve (200), the glove (100) is positioned in a vertical orientation with the finger sleeves pointed downward and substantially perpendicular to the floor, the unfilled test glove is inserted into the glove (100) taking care to ensure the fingertips of the test glove are in contact with the internal surface of the distal end (204, 304, 404, 504, 604) of each sleeve (200, 300, 400, 500, 600), the test glove is then inflated with the specified nitrogen gas to a pressure of 5 psig, and then the measurements are performed as illustrated and described herein. This is also how the panel embodiments are measured, including a panel depth (X25), such as the middle finger sleeve panel depth (425) illustrated in FIG. 7, and a panel width (X35), such as the ring finger sleeve panel width (535) illustrated in FIG. 27. Thus, while certain widths and depths are only illustrated for some sleeves (200, 300, 400, 500, 600), such as those in FIGS. 7, 9, and 27, one skilled in the art will appreciate that the dimensioned and disclosed widths and depths apply equally to each sleeve whether specifically mentioned or not.

Now, referring to the aperture, and aperture aspects, generically so as to apply to any one, or all, of the sleeves (200, 300, 400, 500, 600), the aperture is an opening through the gripping surface (240, 340, 440, 540, 640) so that the external skin (1100) of a finger or thumb is exposed through the aperture, and preferably extends outward through the aperture. All the dimensions of the aperture(s) are measured when the sleeve(s) are occupied with the inflated test glove using the procedure previously outlined. The aperture is located so that majority of the aperture is at, or distal to, the distal interphalangeal joint (1000), seen in FIG. 8, or interphalangeal joint in the case of the thumb, and a portion of the aperture has an aperture width (282, 382, 482, 582, 682), seen in FIGS. 10-15, that is 25-75% of the sleeve width (230, 330, 430, 530, 630), and is 35-65% in another embodiment, and is 45-60% in still a further embodiment. In a further embodiment the greatest aperture length (281, 381, 481, 581, 681) is larger than the greatest aperture width (282, 382, 482, 582, 682), such as the embodiments of FIGS. 3, 4, and 12.

In a further embodiment the greatest aperture length (281, 381, 481, 581, 681) is at least 5% of the sleeve length (210, 310, 410, 510, 610), and in a further embodiment the greatest aperture length is no more than 40% of the sleeve length, and in still another embodiment it is 12.5-30%. In still another embodiment the greatest aperture length (281, 381, 481, 581, 681) is larger than the aperture leading edge offset (284, 384, 484, 584, 684), as seen in the embodiment of FIG. 12, while in a further embodiment the greatest aperture length is no more than three times the aperture leading edge offset, and in still a further embodiment the greatest aperture length is no more than twice the aperture leading edge offset. In still another embodiment the aperture leading edge offset (284, 384, 484, 584, 684) is at least 75% of the greatest aperture width (282, 382, 482, 582, 682), will it is at least 100% in another embodiment, and at least 125% in still a further embodiment. While in still another embodiment the aperture trailing edge offset (285, 385, 485, 585, 685) is less than the sum of the greatest aperture length (281, 381, 481, 581, 681) and the greatest aperture width (282, 382, 482, 582, 682). In one embodiment the open area of each aperture is 0.5-3.0 cm$^2$, while in another embodiment it is 0.6-2.5 cm$^2$, and is 0.7-2.0 cm$^2$ in still a further embodiment, and 0.75-1.5 cm$^2$ in a final embodiment. In a further series of embodiments the aperture perimeter of each aperture has a length of 2.0-7.0 cm, and 2.25-6.0 cm in another embodiment, 2.5-5.0 cm in yet another embodiment, 2.75-4.0 cm in a further embodiment, and 3.0-3.75 cm in a final embodiment. The aperture length is at least 0.5 cm in one embodiment, while the aperture width is at least 0.5 cm in another embodiment, and in a further embodiment at least one of either the length or width is at least 1.0 cm, and at least 1.5 cm in another embodiment, and no more than 3.0 cm in yet another embodiment, and not more than 2.0 cm in still a further embodiment. Removable fingertips and apertures larger than disclosed herein do little, if anything, to enhance sensitivity.

The aperture leading edge offset (284, 384, 484, 584, 684) also provides the convenience of a place for the user to grab and pull to remove the sleeve and/or glove, since the fit will be snug. The aperture may be any number of shapes, as illustrated in the figures, including single sided curvilinear perimeters such as circles and ovals, as seen in FIGS. 12-13, 2-sided button hole configurations as shown in FIGS. 24-25, 3-sided triangles, as seen in FIG. 10, 4-sided polygons, such as FIG. 11, and other multisided polygons, as seen in FIGS. 14-15. In one multisided embodiment, no sides meet at a hard angle, rather the sides are joined at radiused corners having a radius of curvature of at least 1 mm, and at least 2 mm in another embodiment, and at least 3 mm in still another embodiment. In one oval embodiment the major axis is 10-80% greater than the minor axis, and in another embodiment it is 20-70% greater, and in yet a further embodiment it is 30-60% greater. In one particular embodiment the aperture leading edge offset (284, 384, 484, 584, 684) are 7-30 mm, and are 10-25 mm in another embodiment.

Figure 8:
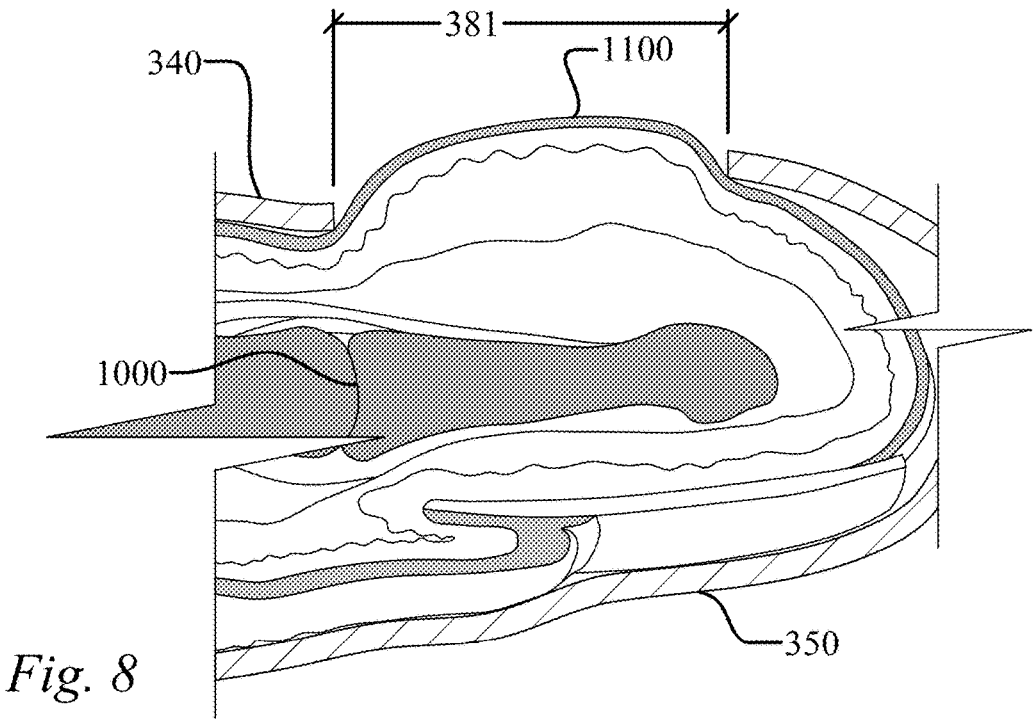
FIG. 8 is a cross-sectional view of an embodiment of a glove finger portion and finger taken along section line 8-8 in FIG. 3, not to scale.

The size and shape of the aperture(s), relationships among the aperture variables, as well as the tightness of the finger sleeve in the vicinity of the aperture, significantly influence the benefits associated with the invention in part by controlling the amount of tissue that projects from the aperture, or is extends proud compared to the adjacent surfaces of the finger sleeve, as seen in FIGS. 8-9. The tissue protrusion also causes a compression of the tissue housing the nerve ending, making the tissue in the area of the aperture perimeter even more sensitive. In some embodiments the construction and size of the of the aperture serves to isolate a small portion of the volar aspect of the skin (1100) and subcutaneous tissue typically located in the middle of the pad overlying the volar aspect of the distal phalange. The tightness of the finger sleeve, and the profile of the change of the tightness of the finger sleeve, is influenced at least in part by changes in the sleeve depth, sleeve width, length, circumference, and/or volume, throughout the sleeve length.

It is not uncommon for prior art gloves to have finger sleeves that taper significantly within the 15 mm nearest the distal end (204, 304, 404, 504, 604), seen in FIG. 2, and therefore the embodiments of this paragraph focus on the changes in the sleeve depth and width in a region of the sleeve referred to as the sleeve primary portion, which is that portion of the sleeve that does not include the most distal 15 mm of the sleeve. In one embodiment the sleeve primary portion has two cross-sections, namely a distal cross-section and a proximal cross-section, that are perpendicular to the longitudinal axis of the sleeve and separated by a distance of 20 mm, and the sleeve width of the cross-section nearest the sleeve distal end, and still within the sleeve primary portion, will be referred to as a distal cross-section, and it is at least 2.5% less than the sleeve width of the proximal cross-section, while in a further embodiment it is at least 5% less than the sleeve width of the proximal cross-section, and in still another embodiment it is at least 7.5% less than the sleeve width of the proximal cross-section, and in a final embodiment it is at least 10% less than the sleeve width of the proximal cross-section. However, another series of embodiments discovers a ceiling on the range, and in one embodiment the sleeve width of the distal cross-section is at most 40% less than the sleeve width of the proximal cross-section, while in another embodiment it is at most 35% less than the sleeve width of the proximal cross-section, and in still a further embodiment it is at most 30% less than the sleeve width of the proximal cross-section.

One particular embodiment has at least one finger sleeve in which the distal cross-section sleeve width is the substantially the same as the proximal cross-section sleeve width, while another embodiment has at least two finger sleeves in which the distal cross-section sleeve width is the substantially the same as the proximal cross-section sleeve width, one if which is the index finger sleeve. In another embodiment the circumference at the distal cross-section, is at least 2.5% less than the circumference of the proximal cross-section, while in a further embodiment it is at least 5% less than the circumference of the proximal cross-section, and in still another embodiment it is at least 7.5% less than the circumference of the proximal cross-section, and in a final embodiment it is at least 10% less than the circumference of the proximal cross-section. However, another series of embodiments discovers a ceiling on the range, and in one embodiment the circumference at the distal cross-section is at most 40% less than the circumference at the proximal cross-section, while in another embodiment it is at most 35% less than the circumference of the proximal cross-section, and in still a further embodiment it is at most 30% less than the circumference of the proximal cross-section.

In yet another embodiment the average circumference of cross-sections spaced 5 mm apart and occurring in an aperture zone, which is the region 15 mm on each side (distal and proximal) of a centroid of an aperture, is less than 5.6 cm. For example, the centroid of an aperture is located and a first cross-sectional circumference is measured, then three additional cross-sectional circumferences are measured, every 5 mm, toward the distal end, and three additional cross-sectional circumferences are measured, every 5 mm toward the proximal end, for a total of seven circumferences in the aperture zone, which when averaged produce an average circumference of less than 5.4 cm, which in a further embodiment is less than 5.1 cm, and in still a further embodiment is less than 4.8 cm, and in yet another embodiment is less than 4.5 cm. For example, looking at the index finger sleeve of FIG. 3, first the centroid of the aperture (380) is found and an index finger aperture centroid cross-section is identified, and represented at section line 9-9, and a circumference of the finger sleeve is measured at this cross-section. Then three additional cross-sections are taken starting 5 mm from the index finger aperture centroid cross-section, and spaced 5 mm from each other, in the direction of the distal end of the index finger sleeve, and similarly three additional cross-sections are taken starting 5 mm from the index finger aperture centroid cross-section, and spaced 5 mm from each other, in the direction of the proximal end of the index finger sleeve. Thus, one can imagine section line 9-9 being offset 5 mm to 3 locations toward the distal end, and being offset 5 mm to 3 locations toward the proximal end, and a circumference measured at each of the seven cross-sections, and the seven circumferences are averaged to produce an average index finger aperture zone circumference. A further embodiment continues to measure cross-sectional circumferences outside of the aperture zone, still every 5 mm, until the sleeve proximal and distal ends are reached, and the average cross-sectional circumference outside of the aperture zone, which may be referred to as the average non-aperture zone circumference, is at least 2.5% greater than the average circumference within the aperture zone, which is at least 5% greater in a further embodiment, and at least 7.5% greater in still another embodiment. In another series of embodiments the average cross-sectional circumference outside of the aperture zone is no more than 25% greater than the average circumference within the aperture zone, which is no more than 20% greater in a further embodiment, no more than 15% greater in still another embodiment, and no more than 12.5% greater in still another embodiment.

Another series of embodiments adds a third cross-section, namely a second proximal cross-section that is separated from the proximal cross-section by a distance of 20 mm, and the sleeve width of the proximal cross-section is at least 2.5% less than the sleeve width of the second proximal cross-section, while in a further embodiment it is at least 5% less than the sleeve width of the second proximal cross-section, and in still another embodiment it is at least 7.5% less than the sleeve width of the second proximal cross-section, and in a final embodiment it is at least 10% less than the sleeve width of the second proximal cross-section. However, another series of embodiments discovers a ceiling on the range, and in one embodiment the sleeve width of the proximal cross-section is at most 40% less than the sleeve width of the second proximal cross-section, while in another embodiment it is at most 35% less than the sleeve width of the second proximal cross-section, and in still a further embodiment it is at most 30% less than the sleeve width of the second proximal cross-section. In another embodiment the change in the sleeve width between the second proximal cross-section and the proximal cross-section is not the same as the change in the sleeve width between the proximal cross-section and the distal cross-section; and in a further embodiment the change in the sleeve width between the proximal cross-section and the distal cross-section is greater than the change in the sleeve width between the second proximal cross-section and the proximal cross-section, while in still a further embodiment it is at least 5% greater, and at least 10% greater in another embodiment, and at least 15% greater in still a further embodiment.

Unlike the embodiment shown in FIG. 9, in one embodiment the thumb sleeve aperture (280) is not centered at the midpoint of the sleeve width (330), or the panel width (535), but is eccentric and angled toward the palm area of the glove (110). In these figures the aperture is located directly above the centroid of the cross-sectional area, or at the 12 o'clock position, with reference to an imaginary line perpendicular to a reference location. The reference location is the average centroid of the finger nail, taken from a pool of 100 users with hands that fit snuggly in the glove (100), which establishes the 12 o'clock position in FIGS. 9 and 27. One embodiment of the thumb sleeve has the aperture centroid located between the 8 and 12 o'clock position, while in another embodiment it is between the 9 and 11 o'clock positions.

Now, turning our attention to the sleeve depth with reference to the same cross-sections just discussed, in one embodiment the sleeve depth of the distal cross-section is at least 2.5% less than the sleeve depth of the proximal cross-section, while in a further embodiment it is at least 5% less than the sleeve depth of the proximal cross-section, and in still another embodiment it is at least 7.5% less than the sleeve depth of the proximal cross-section, and in a final embodiment it is at least 10% less than the sleeve depth of the proximal cross-section. However, another series of embodiments discovers a ceiling on the range, and in one embodiment the sleeve depth of the distal cross-section is at most 40% less than the sleeve depth of the proximal cross-section, while in another embodiment it is at most 35% less than the sleeve depth of the proximal cross-section, and in still a further embodiment it is at most 30% less than the sleeve depth of the proximal cross-section. One particular embodiment has at least one finger sleeve in which the distal cross-section sleeve depth is the substantially the same as the proximal cross-section sleeve depth, while another embodiment has at least two finger sleeves in which the distal cross-section sleeve depth is the substantially the same as the proximal cross-section sleeve depth, one if which is the index finger sleeve.

Another series of embodiments the sleeve depth of the proximal cross-section is at least 2.5% less than the sleeve depth of the second proximal cross-section, while in a further embodiment it is at least 5% less than the sleeve depth of the second proximal cross-section, and in still another embodiment it is at least 7.5% less than the sleeve depth of the second proximal cross-section, and in a final embodiment it is at least 10% less than the sleeve depth of the second proximal cross-section. However, another series of embodiments discovers a ceiling on the range, and in one embodiment the sleeve depth of the proximal cross-section is at most 40% less than the sleeve depth of the second proximal cross-section, while in another embodiment it is at most 35% less than the sleeve depth of the second proximal cross-section, and in still a further embodiment it is at most 30% less than the sleeve depth of the second proximal cross-section. In another embodiment the change in the sleeve depth between the second proximal cross-section and the proximal cross-section is not the same as the change in the sleeve depth between the proximal cross-section and the distal cross-section; and in a further embodiment the change in the sleeve depth between the proximal cross-section and the distal cross-section is greater than the change in the sleeve depth between the second proximal cross-section and the proximal cross-section, while in still a further embodiment it is at least 5% greater, and at least 10% greater in another embodiment, and at least 15% greater in still a further embodiment.

Again using the test glove setup and configuration, in one embodiment the total open area per sleeve does not exceed 20% of that particular sleeve's surface area, while in another embodiment it does not exceed 15%, and in yet another embodiment it does not exceed 10%. Further, in another series of embodiments the total open area on any one sleeve is at least 3% of that particular sleeve's surface area, while in another embodiment it at least 5%, and in yet another embodiment it is at least 7%. Focusing now only on the gripping surface area of a sleeve, as opposed to the dorsum side surface area or total sleeve surface area, in one embodiment the total open area per sleeve does not exceed 35% of that particular sleeve's gripping surface area, while in another embodiment it does not exceed 25%, in yet another embodiment it does not exceed 20%, and in a final embodiment does not exceed 15%. Further, in another series of embodiments the total gripping surface open area on any one sleeve is at least 4% of that particular sleeve's gripping surface area, while in another embodiment it at least 5%, and in yet another embodiment it is at least 7%. Preferably, in one embodiment any one sleeve preferably has a total open area of 0.5-6.0 cm2, while in another embodiment it is 0.5-5.0 cm2, and is 0.5-4.0 cm2 in still a further embodiment, and 0.5-3.0 cm2 in a yet another embodiment.

Figure 5:
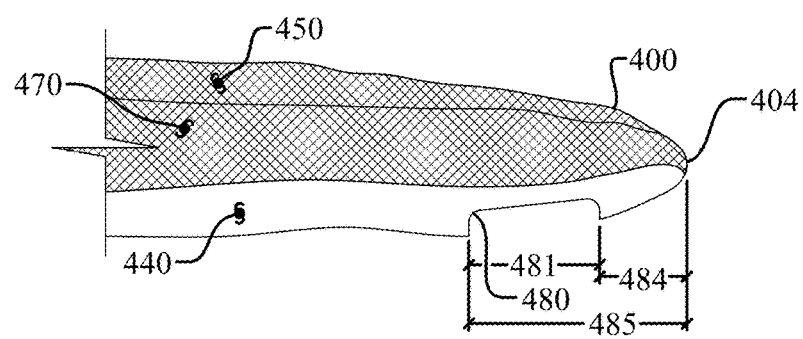
FIG. 5 is a sectional view of an embodiment of a glove finger portion taken along section line 5-5 in FIG. 2, not to scale.
Figure 6:
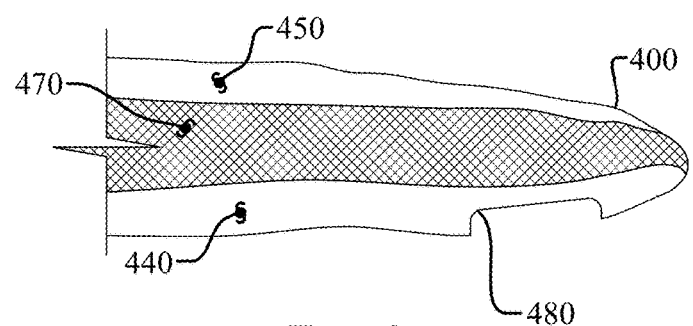
FIG. 6 is a sectional view of an embodiment of a glove finger portion taken along section line 5-5 in FIG. 2, not to scale.
Figure 7:
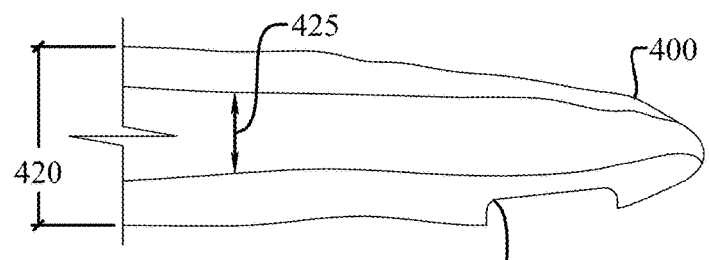
FIG. 7 is a sectional view of an embodiment of a glove finger portion taken along section line 5-5 in FIG. 2, not to scale.

The variations in the sleeve width, depth, length, circumference, and/or volume, balance the benefits associated with controlling the amount of tissue that projects from the aperture, as seen in FIGS. 8-9, while not imparting discomfort to the user due to excessive compression of the thumb and/or fingers, and not adversely impacting circulation and/or unduly compressing and influencing the arteries, veins, and nerves of the thumb and fingers. In addition to the variations discussed, additional embodiments may incorporate at least one elastic element such as a thumb sleeve elastic element (290), an index finger sleeve elastic element (390), a middle finger sleeve elastic element (490), a ring finger sleeve elastic element (590), and/or a small finger sleeve elastic element (690), as illustrated in FIGS. 16-21. The elastic element may be adjacent to, or surrounding, at least a portion of the aperture, as in FIGS. 16-21, or a more significant portion of the finger sleeve may form the elastic element including even a majority of a finger sleeve side surface (dorsum, sinistral, or dextral) as seen in FIGS. 5-6. The elastic element may provide a localized tightness, or reduced cross-sectional area, circumference, width, depth, and/or length of the sleeve, in the vicinity of the aperture to further increase the projection of the tissue through the aperture.

In one at least one of the thumb sleeve (200) and the finger sleeves (300, 400, 500, 600) are configured such that the compressive pressure on the associated finger of the test glove, at a location 25 mm from the distal end (204, 304, 404, 504, 604) along the gripping surface (240, 340, 440, 540, 640) is greater than 10 mm Hg, while in a further embodiment it is greater than 20 mm Hg, while in a further embodiment it is greater than 30 mm Hg, while in a further embodiment it is greater than 40 mm Hg, and in still a further embodiment it is greater than 50 mm Hg. In another series of embodiments the compressive pressure on the associated finger of the test glove, at a location 25 mm from the distal end (204, 304, 404, 504, 604) along the gripping surface (240, 340, 440, 540, 640) is no greater than 70 mm Hg, no greater than 60 mm Hg in another embodiment, and no greater than 50 mm Hg in a further embodiment. The compressive pressure is measured with the aperture covered with material matching that adjacent to the aperture; preferably a small section of the finger sleeve is removed from the dorsum side surface and trimmed to cooperate with the shape of the aperture, and then sewn into the aperture. The compressive pressure is measured via a 1 cm by 1 cm flexible sensor centered at the midpoint of the sleeve width. The sensor is a medical pressure measurement devices such as the Kikuhime®, SIGaT-Tester®, Picopress®, or Pliance X® apparatus, or commercially available pressure and force sensors able to consistently measure very low pressure levels and being thin and flexible, such as the Peratech QTC™, Interlink FSR®, Sensitronics®, Tactilus®, and Tekscan Flexiforce®, which are often thin and flexible piezoresistive force sensors.

Further, the sleeve length (210, 310, 410, 510, 610) also plays a significant role in controlling the amount of tissue that projects from the aperture, as seen in FIGS. 8-9, while not imparting discomfort to the user due to excessive compression of the thumb and/or fingers, and not adversely impacting circulation and/or unduly compressing and influencing the arteries, veins, and nerves of the thumb and fingers. The present sleeve length (210, 310, 410, 510, 610) is less than that of traditional gloves in order to serve a purpose, which unlike traditional gloves is not comfort. Rather, having a sleeve length (210, 310, 410, 510, 610) that is less than the length of the associated digit that will be placed within the sleeve, minimizes the risk of loose excess material extending beyond the end of the digit, and increases the likelihood that the end of the digit will be wedged into the distal end of the finger sleeve, thereby achieving the desired compression of the tissue beyond the distal interphalangeal joint, presentment of the tissue through the aperture, and reduction of the sensitivity of the compressed and non-exposed portions of the hand. In some embodiments the sleeves are designed to increase in length (210, 310, 410, 510, 610) by at least 2.5 mm when a tensile load of 2.5 lbf is applied to the sleeve distal end, which may be accomplished via an elastic element (390) extending around the sleeve, as seen in the embodiments of FIGS. 17-19. In a further embodiment the increase in length (210, 310, 410, 510, 610) is no more than 7.5 mm, and no more than 5 mm in still a further embodiment. Thus, the compressive pressure may be a product of the variation in the sleeve width, depth, length, elastic element(s), circumference, cross-sectional area, and/or volume. In one embodiment the overall sleeve lengths (210, 310, 410, 510, 610) measured using the test glove procedure previously defined, are 50-95 mm, 55-90 mm in another embodiment, and 55-85 in a further embodiment. In another embodiment the sleeve widths (230, 330, 430, 530, 630) are 15-25 mm, and 17-23 mm in another embodiment, while a further embodiment has at least two sleeves with sleeve widths of at least 20 mm. In another embodiment the sleeve depths (220, 320, 420, 520, 620) are 15-25 mm, 17-23 mm in another embodiment, and another embodiment has at least two sleeves having sleeve depths of at least 20 mm. Further, the aperture size and location also plays a significant role in the amount of the external skin (1100) of a finger or thumb that is exposed through the aperture and captured by the aperture to promote that it is extending outward through the aperture.

Figure 31:
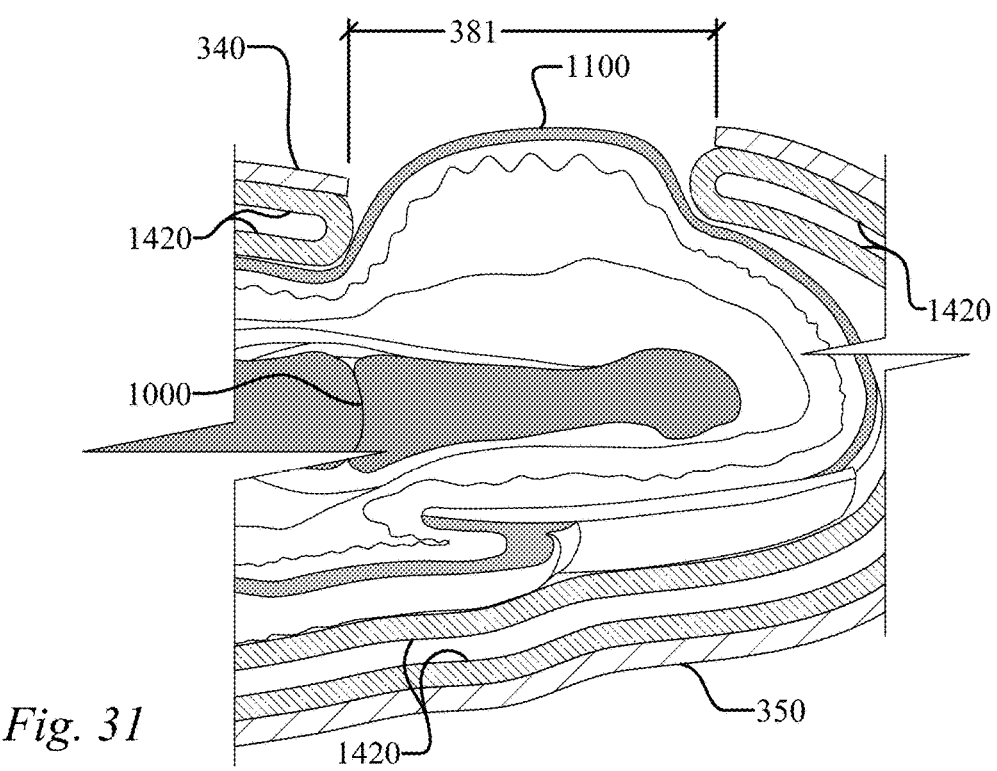
FIG. 31 is a cross-sectional view of an embodiment of a glove finger portion having a bladder and finger, not to scale.

The variations in the aperture size, location, sleeve width and depth, volume, circumference, and/or cross-sectional area, balance the benefits associated with controlling the amount of tissue that projects from the aperture while not imparting discomfort to the user due to excessive compression of the thumb and/or fingers, and not adversely impacting circulation and/or unduly compressing and influencing the arteries, veins, and nerves of the thumb and fingers. In addition to the variations discussed, additional embodiments may incorporate a compression system (1300), such as the examples illustrated in FIGS. 30-33, which may be adjustable and allow the user to easily control the compressive pressure. One such embodiment incorporates a pump compression system (1400), which may include a pump (1410) in fluid communication with a bladder (1420). As seen in FIG. 31, in one embodiment the bladder (1420) is incorporated as a portion of one or more sleeves essentially creating a double-walled portion of the sleeve whereby the exterior wall is non-elastic and increasing the pressure of air, or fluid, between the walls, as a result of the pump (1410), applies the previously disclosed compressive pressure on the user's digit. The bladder (1420) may surround majority of the cross-sectional perimeter of a sleeve like in the embodiment of FIG. 31, or the bladder (1420) may simply consist of one or more smaller chambers within the glove (100), which when inflated increase the distance between an exterior surface of a sleeve and the occupying digit and thereby applying the previously disclosed compressive pressure on a portion of the digit, as illustrated on the index finger sleeve (300) and middle finger sleeve (400) in FIG. 33. For example, in one such embodiment the bladder (1420) may be secured to, or built within, the dorsum side surface of the sleeve, and designed to be substantially flat and undetectable when uninflated but can quickly inflate to have a cross-sectional height dimension of at least 2 mm, and at least 3 mm in another embodiment, and at least 4 mm in still another embodiment. In still a further embodiment the inflated cross-sectional width dimension is greater than the cross-sectional height dimension, which in one embodiment is at least 3 mm, and at least 4 mm in another embodiment, and at least 5 mm in still another embodiment. The length of the tubular bladder (1420) embodiments is preferably at least 5 mm, and at least 10 mm in another embodiment, and at least 15 mm in still a further embodiment. The pump (1410) may be located anywhere on the glove (100), and in one embodiment is no more than a reservoir of greater volume than the bladder (1420), wherein the reservoir is positioned within the glove (100) such that when an object is grasped in a certain manner, such as when gripping a golf club, bat, baseball bat, etc., the reservoir is compressed and forces fluid into the bladder (1420), thereby producing the compressive pressure and all the associated results and benefits. Thus, the compression system (1400) may act directly on a digit, as seen in FIG. 31, or may indirectly act on the digit by forcing a portion of the sleeve away from the digit, which then results in the compressive pressure on the opposite side of the digit.

Figure 32:
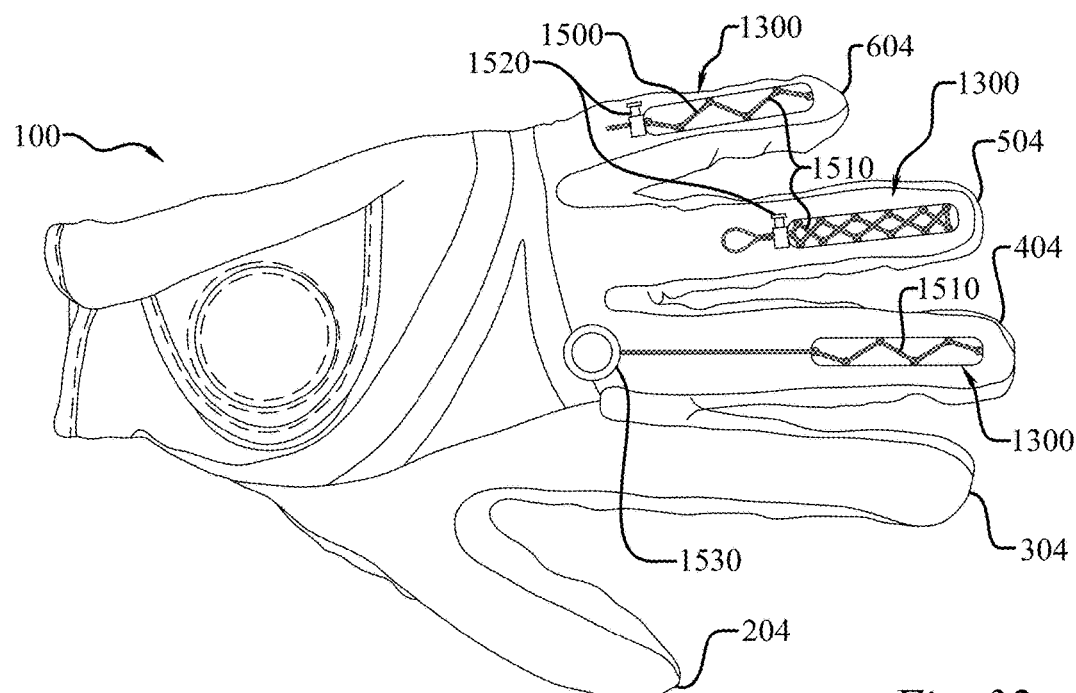
FIG. 32 is a top plan view of an embodiment of a glove with various compression systems, not to scale.
Figure 33:
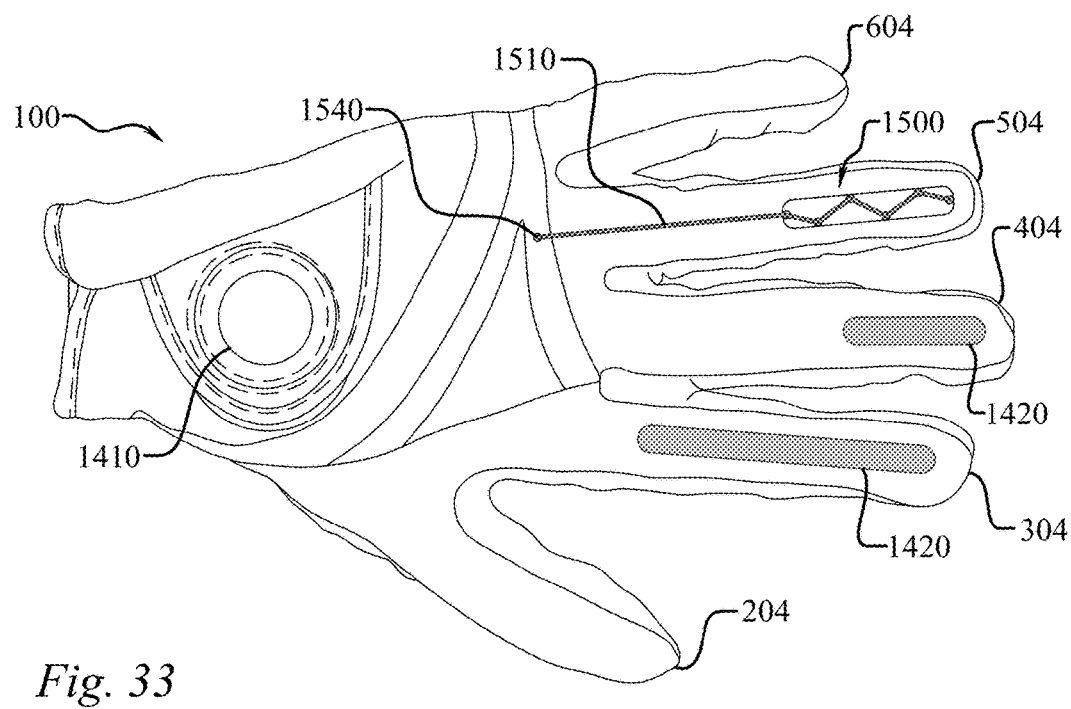
FIG. 33 is a top plan view of an embodiment of a glove with various compression systems, not to scale.

Further, the disclosed desired compressive pressure in the vicinity of an aperture may also be achieved via a drawstring system (1400), such as the embodiments of FIGS. 32 and 33. The drawstring system (1500) may incorporate a drawstring (1510) and a locking device (1520). The drawstring (1510) may be threaded in a single weave pattern through a series of eyelets, as seen on the small finger sleeve of FIG. 32, or it may be a crisscross weave pattern, similar to a shoe lacing system, as seen on the ring finger of FIG. 32, both of which may incorporate a locking device (1520) to secure a particular tension within the drawstring (1510), which produces the disclosed desired compressive pressure adjacent the aperture. One particular embodiment introduces a tightening mechanism (1530), seen on the middle finger sleeve of FIG. 32, to ease the process of tightening the drawstring (1510) and securing it in place. In one embodiment the tightening mechanism (1530) is a rotary locking device that winds and locks the drawstring (1510) to introduce the compressive pressure while only needing the dexterity of two fingers on the opposite hand. One skilled in the art will appreciate that a linear slide tightening mechanism (1530) may also be incorporated. In some embodiments the drawstring (1510) is non-elastic, while in some embodiments the drawstring (1510) has a limited degree of elasticity. One embodiment simply orients and anchors the drawstring (1510) to a portion of the glove (100) so that as a first is made, or the fingers are bent to grasp an object, the drawstring (1510) tightens the sleeve and creates the compressive pressure. For example, one such embodiment is illustrated on the ring finger sleeve in FIG. 33 where the drawstring (1510) extends internally or externally from the ring finger sleeve on the dorsum side (120) of the glove (100) to a drawstring anchor (1540) located external to the sleeve, which in one embodiment is located past the knuckle location. Thus, as an object is grasped and the fingers bent to a grasping position in the direction of making a fist, the drawstring (1510) is fixed at the anchor (1540) and results in the cinching of the finger sleeve, thereby imparting the compressive pressure in the vicinity of the aperture.

Additionally, the disclosed and desired compressive pressure, and resulting results, may be achieved via a method of custom fitting a glove (100), and/or sleeve, to the hand or digits of a particular user. In one embodiment the volume of one or more digits of a user's hand, or hands, is measured, which may be accomplish via optical or electronic scanning, or older technologies including, but not limited to, water displacement techniques. In another embodiment the circumference, cross-sectional area, length, width, and/or depth of one or more digits of a user's hand, or hands, is measured, which may be accomplish via optical or electronic scanning, or older technologies including, but not limited to, string and tape based measurement techniques. One particular embodiment includes a custom fitting method in which the aperture size and shape are custom tailored to a particular user in light of the length, width, and/or depth of the user's distal phalange for the thumb and/or finger(s). In a further embodiment the aperture width is at least 50% of the width of the user's distal phalange, and in yet another embodiment the aperture length is at least 50% of the length of the user's distal phalange. The size and shape of the aperture(s), relationships among the aperture variables, as well as the tightness of the finger sleeve in the vicinity of the aperture, significantly influence the benefits associated with the invention in part by controlling the amount of tissue that projects from the aperture, or is extends proud of the adjacent surfaces of the finger sleeve, as seen in FIGS. 8-9. As previously touched upon, the tissue protrusion also causes a compression of the tissue housing the nerve ending, making the tissue in the area of the aperture perimeter even more sensitive. In some embodiments the construction and size of the of the aperture serves to isolate a small portion of the volar aspect of the skin (1100) and subcutaneous tissue typically located in the middle of the pad overlying the volar aspect of the distal phalange. The tightness of the finger sleeve, and the profile of the change of the tightness of the finger sleeve, is influenced at least in part by changes in the sleeve depth, sleeve width, length, circumference, and/or volume, throughout the sleeve length. Therefore, in one embodiment a plurality of these variables are adjusted so that a portion of the skin (1100) extending through the aperture is at least 1 mm beyond the elevation of the adjacent exterior surface of the sleeve at the aperture perimeter, or 1 mm proud, while in another embodiment it is at least 2 mm proud, and in yet a further embodiment it is at least 3 mm proud. However, an additional series of embodiments established an upper limit to how far a portion of the skin (1100) extends through the aperture and beyond the elevation of the adjacent exterior surface of the sleeve at the aperture perimeter, or how far proud it projects, due to diminishing sensitivity returns and eventual negative influence of an excessively tight fit. Thus, in another embodiment no portion of the skin (1100) is more than 7 mm proud of the aperture, while in another embodiment it is no more than 5.5 mm proud of the aperture, and in still another embodiment it is no more than 4.0 mm proud of the aperture. Therefore, further custom fitting embodiments are directed to adjusting the variables to achieve the proud projection of the skin (1100) through the aperture within the disclosed ranges for preferential enhanced sensitivity.

A further series of embodiments appreciates the importance of the aperture size but additionally recognizes criticality of exerting the compressive pressure on the digit in the area of the aperture to ensure a portion of the digits extends through the aperture and proud, or protruding from, the sleeve. Therefore, in one embodiment at least a portion of the custom fitted sleeve width is at least 2.5% less than the measured width of the digit at the corresponding location, at least 5% less in another embodiment, and at least 7.5% less in still a further embodiment. A further series of embodiments recognizes the diminishing benefits and introduction of negative effects associated with too tight a fit and therefore no portion of the custom fitted sleeve width is more than 12.5% less than the measured width of the digit at the corresponding location, and no more than 10% less in another embodiment, and no more than 7.5% less in still a further embodiment. Similarly, in one embodiment at least a portion of the custom fitted sleeve depth is at least 2.5% less than the measured depth of the digit at the corresponding location, at least 5% less in another embodiment, and at least 7.5% less in still a further embodiment. A further series of embodiments recognizes the diminishing benefits and introduction of negative effects associated with too tight a fit and therefore no portion of the custom fitted sleeve depth is more than 12.5% less than the measured depth of the digit at the corresponding location, and no more than 10% less in another embodiment, and no more than 7.5% less in still a further embodiment. Additionally, in one embodiment the custom fitted sleeve length is at least 2.5% less than the measured length of the digit, at least 5% less in another embodiment, and at least 7.5% less in still a further embodiment. A further series of embodiments recognizes the diminishing benefits and introduction of negative effects associated with too tight a fit and therefore the custom fitted sleeve length is no more than 12.5% less than the measured width of the digit at the corresponding location, and no more than 10% less in another embodiment, and no more than 7.5% less in still a further embodiment. Similarly, in one embodiment the volume of the custom fitted sleeve is at least 2.5% less than the measured volume of the digit, at least 5% less in another embodiment, and at least 7.5% less in still a further embodiment. A further series of embodiments recognizes the diminishing benefits and introduction of negative effects associated with too tight a fit and therefore the volume of the custom fitted sleeve is more than 12.5% less than the measured volume of the digit, and no more than 10% less in another embodiment, and no more than 7.5% less in still a further embodiment. Additionally, in one embodiment at least a portion of the custom fitted sleeve has a circumference that is at least 2.5% less than the measured circumference of the digit at the corresponding location, at least 5% less in another embodiment, and at least 7.5% less in still a further embodiment. A further series of embodiments recognizes the diminishing benefits and introduction of negative effects associated with too tight a fit and therefore no portion of the custom fitted sleeve has a circumference that is more than 12.5% less than the measured circumference of the digit at the corresponding location, and no more than 10% less in another embodiment, and no more than 7.5% less in still a further embodiment. In still a further embodiment the measurement of one or more aspects of the hand and the creation of the custom fitted glove is performed at a standalone automated kiosk.

Figure 28:
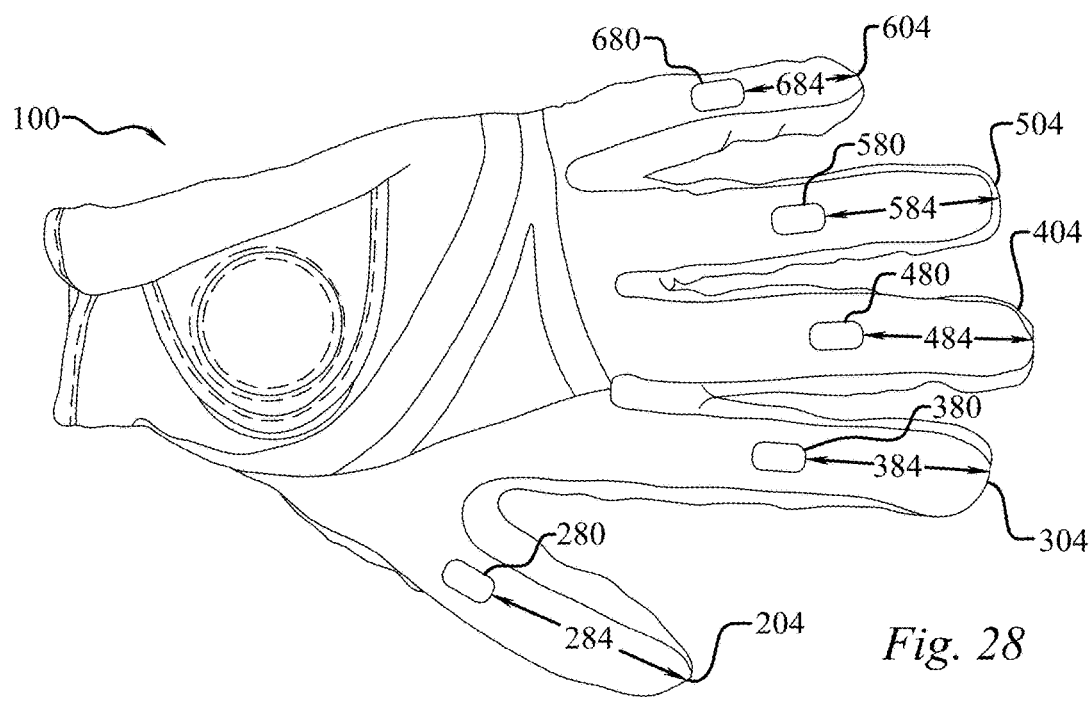
FIG. 28 is a top plan view of an embodiment of a glove, not to scale.
Figure 29:
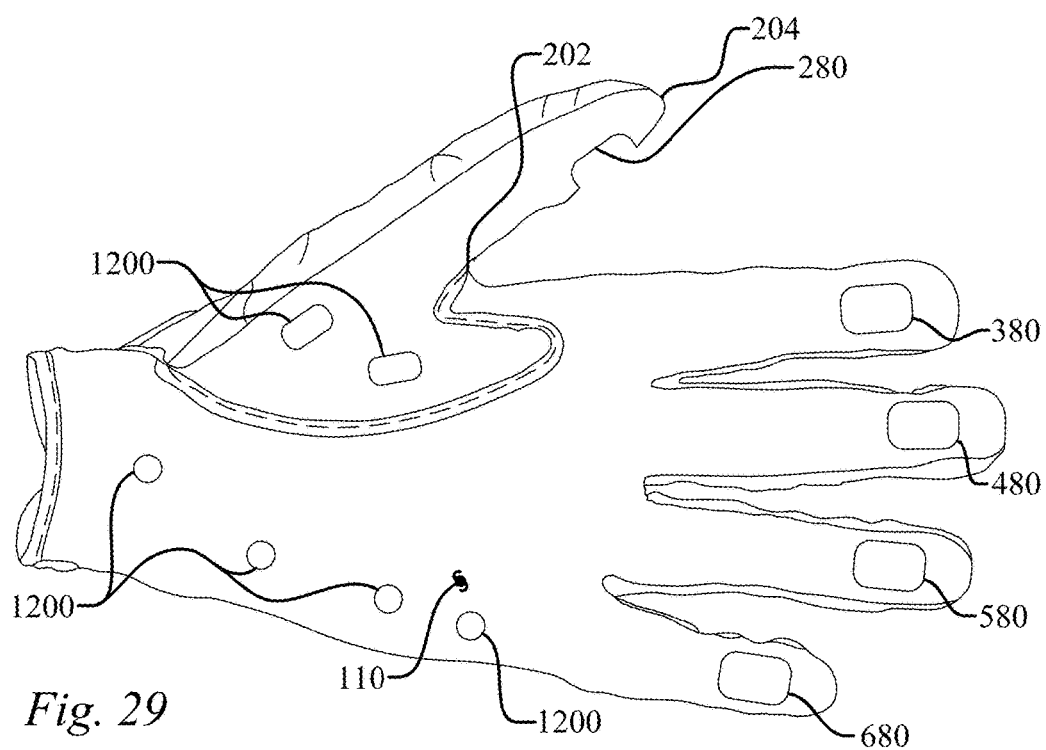
FIG. 29 is a bottom plan view of the embodiment an embodiment of a glove, not to scale.
Figure 30:
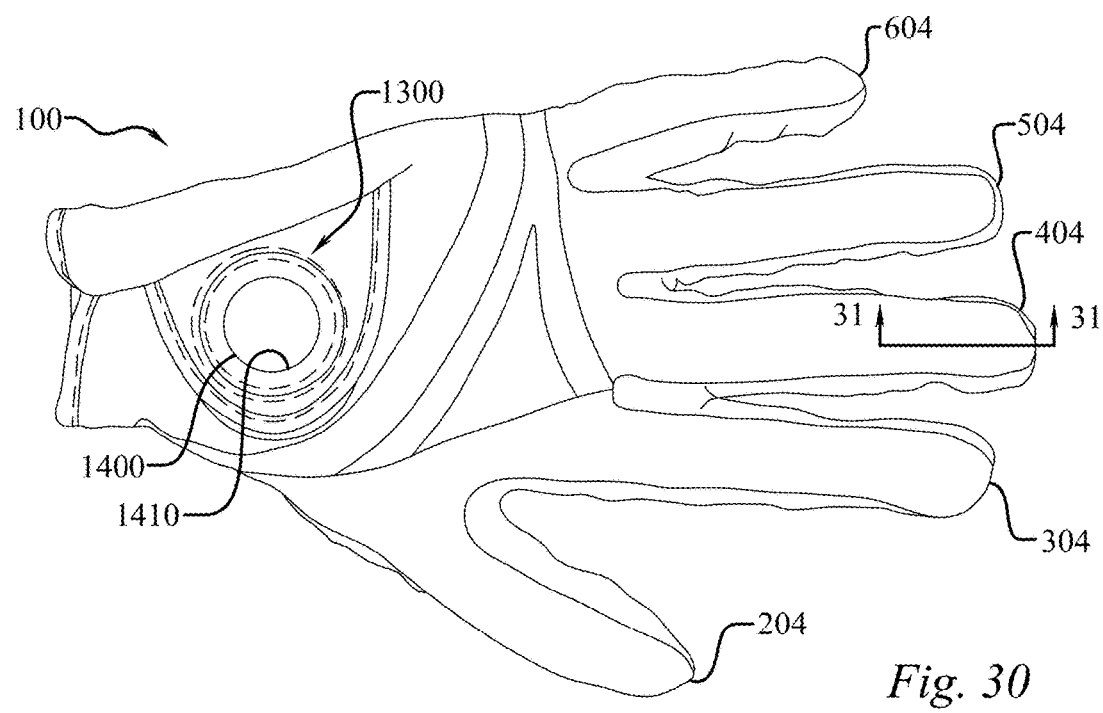
FIG. 30 is a top plan view of an embodiment of a glove, not to scale.

All of the disclosure herein applies equally to embodiments having one or more of the apertures on the dorsum side (120) of the glove (100), including the sleeves, as seen in FIG. 28. Similarly, all of the disclosure herein applies equally to embodiments having one or more of the apertures on the palm side (110) of the glove (100) in areas other than the sleeves, such as the palm apertures (1200) seen in FIG. 29. One particular embodiment incorporates a plurality of palm apertures (1200) on the surface of the glove (100) that houses the thenar eminence, while a further embodiment incorporates a plurality of palm apertures (1200) on the surface of the glove (100) that houses the hypothenar eminence, while in yet another embodiment no palm apertures (1200) are on the surface of the glove (100) that houses the portion of the palm that is distal to the distal traverse, and in still a further embodiment no palm apertures (1200) are on the surface of the glove (100) that houses the portion of the palm that is distal to the proximal traverse. One embodiment has at least two, and no more than five, palm apertures (1200) on the surface of the glove (100) that houses the thenar eminence, and a further embodiment has at least two, and no more than five, palm apertures (1200) on the surface of the glove (100) that houses the hypothenar eminence. Preferably sum of the open surface area associated with the palm apertures (1200) is no more than 10% of the surface area of the palm side (110) of the glove (100) when excluding the sleeves, and no more than 7.5% in a further embodiment, and 2-7.5% in yet another embodiment.

Each of the disclosed relationships associated with the aperture and sleeve sizes, and locations, play a critical role in improving the sensitivity of the exposed areas and reducing the sensation of the covered skin areas, all the while balancing the negative consequences associated with regions that are too tight. Increasing the relative sensitivity of the control hand for throwing or grasping a handle or object, enhances the neurosensory input that results in enhanced proprioception; the body's recognition of its position in space. The enhanced proprioception enhances the likelihood that user can more consistently and accurately perform throwing, hitting, shooting, grasping, and/or controlling remote instruments. The basis for the increased sensitivity is an accentuation of the normal difference of sensitivity between the finger tips and the palm of the hand, with the sensitivity generally being twice as great in the finger tips. This is determined by medical examination testing of two point discrimination and the medial literature, even very recent discoveries such as those discussed in Pruszynski, J. A. & Johansson, R. S. (2014), *Edge-orientation processing in first-order tactile neurons*, Nature Neurosci, which is incorporated herein entirely by reference. In many embodiments the glove covers and insulates the skin of the remainder of the hand, and especially the palm, and results in a relative difference in sensitivity being perceived as much greater on the same side fingertip pads as compared to the opposite hand. This has been repeated demonstrated to potential users by having them rub the exposed regions of the fingers of the gloved hand together, particularly the thumb and index finger, and compare the experienced heightened sensation with that of the opposite ungloved hand performing the same finger rubbing.

An additional embodiment of the glove (100) may provide the benefits disclosed herein by using a tactile perception enhancing device located in any of the positions of the disclosed apertures. In one embodiment the tactile perception enhancing device consists of a relatively rigid object built into the glove or sleeve to contact one or more of the finger pads over the volar aspect of the distal phalanges. For instance, the tactile perception enhancing device may consist of a bladder (1420), such as that associated with the middle finger sleeve of FIG. 33, but with it is on the gripping surface rather than the dorsum surface, however it is not limited to a bladder and may be stitching or even a rigid object of a size and shape that can be sensed by the finger pads. Thus, this application incorporates U.S. application Ser. No. 15/267,006 by reference, as if entirely reproduced herein, particularly all the disclosure associated with the projections, which apply equally to the tactile perception enhancing device incorporated into the glove or sleeve(s). Incorporating a projection into the pad regions of the sleeve provides similar benefits disclosed in U.S. application Ser. No. 15/267,006, as it will be felt and sensed the same as a projection contacting the pad. In one embodiment the tactile perception enhancing device is a projection extending from the interior surface of a sleeve, which in some embodiments may be an inflatable bladder, while in other embodiments it is a rigid material, having a length of less than 25 mm. The specific dimensions disclosed in U.S. application Ser. No. 15/267,006 are important because they exploit several of the user's normal human body attributes to enable the user to consistently grip or interact with another object and recognize the position of the object in space, thereby improving a user's ability to hit, throw, or maneuver the object with increased accuracy. Thus, the glove enhances users' perception and awareness of the "spatial" relationship of the user's body and the object, allowing for improved performance. These attributes include sensibility, proprioception, and neuromuscular memory. Sensibility is the body's ability to determine fine objects by feel. This ability is measured by what is known as two-point discrimination. Two-point discrimination is defined as the ability to discern that two nearby objects touching the skin are truly two distinct points, not one. The test for two-point discrimination is usually performed utilizing two sharp points. Typically, a person has the most sensibility on their finger pads and lips. A normal measurement for two-point discrimination on the finger pads is a width of 2.0 millimeters to 5.0 millimeters, while other body parts, such as the back, have much larger measurements due to less nerve endings. When the two points are closer together than the range of two-point discrimination a person cannot tell whether they are being contacted by one point or two points. Proprioception is the unconscious perception of movement and spatial orientation arising from stimuli within the body itself. For humans, these stimuli are detected by nerves within the body, such as in joints, tendons, and muscles. A practical example of proprioception is the ability to close one's eyes and touch the index fingers of both hands together without looking. As a result of proprioception, the human body has the ability to know exactly where it is in space. The human body also has the ability to remember and repeat past movements, which are referred to as neuromuscular memory. As sensations are recorded by the body and movements are repeated over time, the body develops an ability to repeat movements without conscious effort.

As previously disclosed, the desired compressive pressure may be a product of the variation in the sleeve width, depth, length, elastic element(s), circumference, cross-sectional area, volume, and/or compression system. In a further embodiment the compression system includes portions of the glove (100) or sleeves that incorporate heat activated shrinkable sleeves, sleeve panels, sleeve portions, elastic elements, aperture reinforcement, drawstrings, or the entire glove (100). The heat activated shrinkable portion may be activated by exposure to a heat source producing a first predetermined activation temperature on the outer surface of the heat activated shrinkable component. Due to the material properties of the heat activated shrinkable portion, it shrinks, thereby reducing the open interior volume, when exposed to the first predetermined activation temperature, forming a tight fit around the area of the body that is to be enclosed, and introducing the disclosed compressive pressure. To further increase the adjustability of the glove (100) or sleeves, another embodiment may include a plurality of tear away stress lines, in the at least one layer of material, thereby imparting adjustability of the volume. In this embodiment, the user may tear away portions of the glove (100) or sleeve(s) along any of the plurality of tear away stress lines, either before or after shrinking to conform to the user, thereby achieving a custom fit. Further, the glove (100) or sleeve(s) may incorporate compression control stress lines designed to separate, or tear, at a predetermined force, thereby preventing a user over-shrinking the glove (100) or sleeve. In one embodiment the predetermined force is directly correlated with the disclosed compressive pressure, and thus preferred sensitivity is achieve without the negative consequences of too tight a fit. The heat activated glove, sleeve(s), and wearables may incorporate virtually any thermally activated shrinking material. The simplest embodiments incorporate shrink films made essentially of PVC, polyolefin, polyethylene, polyester, nylon, or saran; however one with skill in the art can recognize a number of alternative materials. In some embodiments the materials of construction are selected such that the first predetermined activation temperature can be applied with a conventional hair dryer. As such, in this embodiment, the first predetermined activation temperature is between approximately 100 degrees Fahrenheit and 140 degrees Fahrenheit. Further, the material thickness may vary greatly depending on the particular application. However, in one embodiment the material thickness is between approximately 0.25 mil and approximately 35 mil, and between approximately 5 mil and approximately 25 mil in another embodiment, and between approximately 10 mil and approximately 20 mil in yet a further embodiment. Additionally, the shrinkage rate of the glove and/or sleeve(s) is dependent upon the material and the material thickness. The shrinkage rate for one embodiment is between approximately 20 percent and approximately 85 percent. This range allows the creation of a glove and/or sleeve(s) that may be effectively applied to a wide range of sizes.

In one particular embodiment the glove (100) has one sleeve having an aperture, while another embodiment has at least two sleeves with each having an aperture, while a further embodiment has at least three sleeves having an aperture, while yet another embodiment has at least four sleeves having an aperture, and a final embodiment has an aperture on all five sleeves. A further embodiment builds upon any of these prior embodiments by also incorporating at least one palm aperture (1200). Still further embodiments narrow any of the prior embodiments by incorporating only a single aperture per sleeve to further enhance the sensitivity in only that area and avoiding multiple zones of increased sensitivity per digit, which can create conflicting biofeedback and reduce the associated benefits.

The glove (100) and finger sleeves may be beneficial in all sports, including but not limited to, golf, baseball, basketball, baseball, football, racquet and paddle sports, cricket, pool, darts, bowling, archery/firearm shooting, curling, track and field throwing and pole vaulting events, lacrosse, water sports involving paddles and oars such as kayak, rowing, and canoe paddle handles, skiing and water skiing, fishing, fly fishing, bicycling, motorcycling and snowmobiling, martial arts, fencing, juggling, weight lifting, frisbee sports, and acrobatics, just to name a few. Additionally, the glove (100) and sleeves may be incorporated in any activity that benefits from enhanced sensitivity including activities such as typing, reading braille, video gaming, machine operation via contact with a wheel (including motorsports), knob, stick, remote control instrumentation, joy stick, surgery remote control, and/or airplane piloting, just to name a few. This enhanced sensitivity is particularly applicable in the case of an amputated extremity. A liner or sleeve may be worn on an extremity to increase the sensitivity, particularly to enhance that part of the prosthesis used to activate the distal part of the prosthesis. The glove and/or sleev(s) could be customized to a specific patient having partial amputations of fingers or thumb, or a deformity of the hand, to maximize what function remains in the injured body part. Additionally, while the disclosure above is directed to gloves and finger sleeves, one skilled in the art will appreciate that all of the disclosure applies equally to socks, shoes, toe sleeves, and wearables in general, but will not be repeated to avoid excessive duplication. Thus, glove is interchangeable with sock and shoe, toe is interchangeable with finger and/or thumb, and wearables is interchangeable with glove. Numerous alterations, modifications, and variations of the preferred embodiments disclosed herein will be apparent to those skilled in the art and they are all anticipated and contemplated to be within the spirit and scope of the application. For example, although specific embodiments have been described in detail, those with skill in the art will understand that the preceding embodiments and variations can be modified to incorporate various types of substitute and or additional or alternative materials, relative arrangement of elements, and dimensional configurations. Accordingly, even though only few variations are described herein, it is to be understood that the practice of such additional modifications and variations and the equivalents thereof, are within the spirit and scope of the invention.

I claim:

1. A glove (100), comprising:
a thumb sleeve (200) and a middle finger sleeve (400);
the thumb sleeve (200) having a thumb sleeve proximal end (202), a thumb sleeve distal end (204), a thumb sleeve length (210), a thumb sleeve depth (220), a thumb sleeve width (230), a thumb sleeve gripping surface (240), a thumb sleeve dorsum side surface (250), a thumb sleeve sinistral side surface (260), a thumb sleeve dextral side surface (270), and a thumb sleeve aperture (280) defining a passageway through the thumb sleeve gripping surface (240), wherein the thumb sleeve aperture (280) has a thumb sleeve aperture length (281) of 0.5-3.0 cm, a thumb sleeve aperture width (282) of 0.5-3.0 cm, a thumb sleeve aperture perimeter (283), a thumb sleeve aperture leading edge offset (284), and a thumb sleeve aperture trailing edge offset (285); and
the middle finger sleeve (400) having a middle finger sleeve proximal end (402), a middle finger sleeve distal end (404), a middle finger sleeve length (410), a middle finger sleeve depth (420), a middle finger sleeve width (430), a middle finger sleeve gripping surface (440), a middle finger sleeve dorsum side surface (450), a middle finger sleeve sinistral side surface (460), a middle finger sleeve dextral side surface (470), and a middle finger sleeve aperture (480) defining a passageway through the middle finger sleeve gripping surface (440), wherein the middle finger sleeve aperture (480) has a middle finger sleeve aperture length (481) of 0.5-3.0 cm, a middle finger sleeve aperture width (482) of 0.5-3.0 cm, a middle finger sleeve aperture perimeter (483), a middle finger sleeve aperture leading edge offset (484), and a middle finger sleeve aperture trailing edge offset (485), wherein the middle finger sleeve aperture width (482) is at least 25% of the middle finger sleeve width (430), the middle finger sleeve aperture length (481) is 5-40% of the middle finger sleeve length (410), and wherein the middle finger sleeve (400) has a middle finger sleeve primary portion defined as the portion of the middle finger sleeve (400) that excludes the portion within 15 mm of the middle finger sleeve distal end (404), whereby a middle distal cross-section and a middle proximal cross-section pass through the middle finger sleeve primary portion, orthogonal to a longitudinal axis of the middle finger sleeve (400), and separated by a distance of 20 mm with the middle distal cross-section located nearest the middle finger sleeve distal end (404), and (a) the middle finger sleeve width (430) at the middle distal cross-section is 2.5-40% less than the middle finger sleeve width (430) at the middle proximal cross-section, and (b) a first middle finger sleeve circumference at the middle distal cross-section is 2.5-40% less than a second middle finger sleeve circumference at the middle proximal cross-section.

2. The glove (100) of claim 1, wherein the middle finger sleeve aperture length (481) is no more than three times the middle finger sleeve aperture leading edge offset (484).

3. The glove (100) of claim 1, wherein the middle finger sleeve aperture length (481) is at least 1.0 cm.

4. The glove (100) of claim 1, wherein the middle finger sleeve depth (420) at the middle distal cross-section is 2.5-40% less than the middle finger sleeve depth (420) at the middle proximal cross-section.

5. The glove (100) of claim 1, wherein the middle finger sleeve aperture open area does not exceed 20% of the middle sleeve total surface area, and the thumb sleeve aperture open area does not exceed 20% of the thumb sleeve total surface area.

6. The glove (100) of claim 1, wherein an average middle finger aperture zone circumference of seven middle finger cross-sections within a middle finger aperture zone are centered about a middle finger aperture centroid cross-section and spaced 5 mm apart, is less than 5.4 cm, and an average middle finger non-aperture zone circumference is 2.5-20% greater than the average middle finger aperture zone circumference.

7. The glove (100) of claim 1, further including a ring finger sleeve (500) having a ring finger sleeve proximal end (502), a ring finger sleeve distal end (504), a ring finger sleeve length (510), a ring finger sleeve depth (520), a ring finger sleeve width (530), a ring finger sleeve gripping surface (540), a ring finger sleeve dorsum side surface (550), a ring finger sleeve sinistral side surface (560), and a ring finger sleeve dextral side surface (570), wherein the ring finger sleeve (500) has a ring finger sleeve aperture (580) defining a passageway through the ring finger sleeve gripping surface (540), wherein the ring finger sleeve aperture (580) has a ring finger sleeve aperture length (581) of 0.5-3.0 cm, a ring finger sleeve aperture width (582) of 0.5-3.0 cm, a ring finger sleeve aperture perimeter (583), a ring finger sleeve aperture leading edge offset (584), and a ring finger sleeve aperture trailing edge offset (585).

8. The glove (100) of claim 7, wherein the ring finger sleeve aperture width (582) is at least 25% of the ring finger sleeve width (530), the ring finger sleeve aperture length (581) is 5-40% of the ring finger sleeve length (510), the ring finger sleeve (500) has a ring finger sleeve primary portion defined as the portion of the ring finger sleeve (500) that excludes the portion within 15 mm of the ring finger sleeve distal end (504), whereby a ring distal cross-section and a ring proximal cross-section pass through the ring finger sleeve primary portion, orthogonal to a longitudinal axis of the ring finger sleeve (500), and separated by a distance of 20 mm with the ring distal cross-section located nearest the ring finger sleeve distal end (504), and (a) the ring finger sleeve width (530) at the ring distal cross-section is 2.5-40% less than the ring finger sleeve width (530) at the ring proximal cross-section, and (b) a first ring finger sleeve circumference at the ring distal cross-section is 2.5-40% less than a second ring finger sleeve circumference at the ring proximal cross-section.

9. The glove (100) of claim 8, wherein the middle finger sleeve aperture leading edge offset (484) is at least 75% of the middle finger sleeve aperture width (482), and the ring finger sleeve aperture leading edge offset (584) is at least 75% of the ring finger sleeve aperture width (582).

10. A glove (100), comprising:
   a thumb sleeve (200) and a ring finger sleeve (500);
   the thumb sleeve (200) having a thumb sleeve proximal end (202), a thumb sleeve distal end (204), a thumb sleeve length (210), a thumb sleeve depth (220), a thumb sleeve width (230), a thumb sleeve gripping surface (240), a thumb sleeve dorsum side surface (250), a thumb sleeve sinistral side surface (260), a thumb sleeve dextral side surface (270), and a thumb sleeve aperture (280) defining a passageway through the thumb sleeve gripping surface (240), wherein the thumb sleeve aperture (280) has a thumb sleeve aperture length (281) of 0.5-3.0 cm, a thumb sleeve aperture width (282) of 0.5-3.0 cm, a thumb sleeve aperture perimeter (283), a thumb sleeve aperture leading edge offset (284), and a thumb sleeve aperture trailing edge offset (285); and
   the ring finger sleeve (500) having a ring finger sleeve proximal end (502), a ring finger sleeve distal end (504), a ring finger sleeve length (510), a ring finger sleeve depth (520), a ring finger sleeve width (530), a ring finger sleeve gripping surface (540), a ring finger sleeve dorsum side surface (550), a ring finger sleeve sinistral side surface (560), a ring finger sleeve dextral side surface (570), and a ring finger sleeve aperture (580) defining a passageway through the ring finger sleeve gripping surface (540), wherein the ring finger sleeve aperture (580) has a ring finger sleeve aperture length (581) of 0.5-3.0 cm, a ring finger sleeve aperture width (582) of 0.5-3.0 cm, a ring finger sleeve aperture perimeter (583), a ring finger sleeve aperture leading edge offset (584), and a ring finger sleeve aperture trailing edge offset (585), wherein the ring finger sleeve aperture width (582) is at least 25% of the ring finger sleeve width (530), the ring finger sleeve aperture length (581) is 5-40% of the ring finger sleeve length (510), and wherein the ring finger sleeve (500) has a ring finger sleeve primary portion defined as the portion of the ring finger sleeve (500) that excludes the portion within 15 mm of the ring finger sleeve distal end (504), whereby a ring distal cross-section and a ring proximal cross-section pass through the ring finger sleeve primary portion, orthogonal to a longitudinal axis of the ring finger sleeve (500), and separated by a distance of 20 mm with the ring distal cross-section located nearest the ring finger sleeve distal end (504), and (a) the ring finger sleeve width (530) at the ring distal cross-section is 2.5-40% less than the ring finger sleeve width (530) at the ring proximal cross-section, and (b) a first ring finger sleeve circumference at the ring distal cross-section is 2.5-40% less than a second ring finger sleeve circumference at the ring proximal cross-section.

11. The glove (100) of claim 10, wherein the ring finger sleeve aperture length (581) is no more than three times the ring finger sleeve aperture leading edge offset (584).

12. The glove (100) of claim 10, wherein the ring finger sleeve aperture width (582) is at least 1.0 cm.

13. The glove (100) of claim 10, wherein the ring finger sleeve depth (520) at the ring distal cross-section is 2.5-40% less than the ring finger sleeve depth (520) at the ring proximal cross-section.

14. The glove (100) of claim 10, wherein the ring finger sleeve aperture open area does not exceed 20% of the ring sleeve total surface area, and the thumb sleeve aperture open area does not exceed 20% of the thumb sleeve total surface area.

15. The glove (100) of claim 10, wherein an average ring finger aperture zone circumference of seven ring finger cross-sections within a ring finger aperture zone are centered about a ring finger aperture centroid cross-section and spaced 5 mm apart, is less than 5.4 cm, and an average ring finger non-aperture zone circumference is 2.5-20% greater than the average ring finger aperture zone circumference.

16. The glove (100) of claim 10, further including a middle finger sleeve (400) having a middle finger sleeve proximal end (402), a middle finger sleeve distal end (404), a middle finger sleeve length (410), a middle finger sleeve depth (420), a middle finger sleeve width (430), a middle finger sleeve gripping surface (440), a middle finger sleeve dorsum side surface (450), a middle finger sleeve sinistral side surface (460), and a middle finger sleeve dextral side surface (470), wherein the middle finger sleeve (400) has a middle finger sleeve aperture (480) defining a passageway through the middle finger sleeve gripping surface (440), wherein the middle finger sleeve aperture (480) has a middle finger sleeve aperture length (481) of 0.5-3.0 cm, a middle finger sleeve aperture width (482) of 0.5-3.0 cm, a middle finger sleeve aperture perimeter (483), a middle finger sleeve aperture leading edge offset (484), and a middle finger sleeve aperture trailing edge offset (485), wherein the middle finger sleeve aperture length (481) is 5-40% of the middle finger sleeve length (410), and wherein the middle finger sleeve (400) has a middle finger sleeve primary portion defined as the portion of the middle finger sleeve (400) that excludes the portion within 15 mm of the middle finger sleeve distal end (404), whereby a middle distal cross-section and a middle proximal cross-section pass through the middle finger sleeve primary portion, orthogonal to a longitudinal axis of the middle finger sleeve (400), and separated by a distance of 20 mm with the middle distal cross-section located nearest the middle finger sleeve distal end (404), and (a) the middle finger sleeve width (430) at the middle distal cross-section is 2.5-40% less than the middle finger sleeve width (430) at the middle proximal cross-section, and (b) a first middle finger sleeve circumference at the middle distal cross-section is 2.5-40% less than a second middle finger sleeve circumference at the middle proximal cross-section.

17. The glove (100) of claim 16, wherein the middle finger sleeve aperture leading edge offset (484) is at least 75% of the middle finger sleeve aperture width (482), and the ring finger sleeve aperture leading edge offset (584) is at least 75% of the ring finger sleeve aperture width (582).

18. A glove (100), comprising:
a thumb sleeve (200) and a small finger sleeve (600);
the thumb sleeve (200) having a thumb sleeve proximal end (202), a thumb sleeve distal end (204), a thumb sleeve length (210), a thumb sleeve depth (220), a thumb sleeve width (230), a thumb sleeve gripping surface (240), a thumb sleeve dorsum side surface (250), a thumb sleeve sinistral side surface (260), a thumb sleeve dextral side surface (270), and a thumb sleeve aperture (280) defining a passageway through the thumb sleeve gripping surface (240), wherein the thumb sleeve aperture (280) has a thumb sleeve aperture length (281) of 0.5-3.0 cm, a thumb sleeve aperture width (282) of 0.5-3.0 cm, a thumb sleeve aperture perimeter (283), a thumb sleeve aperture leading edge offset (284), and a thumb sleeve aperture trailing edge offset (285); and
the small finger sleeve (600) having a small finger sleeve proximal end (602), a small finger sleeve distal end (604), a small finger sleeve length (610), a small finger sleeve depth (620), a small finger sleeve width (630), a small finger sleeve gripping surface (640), a small finger sleeve dorsum side surface (650), a small finger sleeve sinistral side surface (660), a small finger sleeve dextral side surface (670), and a small finger sleeve aperture (680) defining a passageway through the small finger sleeve gripping surface (640), wherein the small finger sleeve aperture (680) has a small finger sleeve aperture length (681) of 0.5-3.0 cm, a small finger sleeve aperture width (682) of 0.5-3.0 cm, a small finger sleeve aperture perimeter (683), a small finger sleeve aperture leading edge offset (684), and a small finger sleeve aperture trailing edge offset (685), wherein the small finger sleeve aperture width (682) is at least 25% of the small finger sleeve width (630), the small finger sleeve aperture length (681) is 5-40% of the small finger sleeve length (610), and wherein the small finger sleeve (600) has a small finger sleeve primary portion defined as the portion of the small finger sleeve (600) that excludes the portion within 15 mm of the small finger sleeve distal end (604), whereby a small distal cross-section and a small proximal cross-section pass through the small finger sleeve primary portion, orthogonal to a longitudinal axis of the small finger sleeve (600), and separated by a distance of 20 mm with the small distal cross-section located nearest the small finger sleeve distal end (604), and (a) the small finger sleeve width (630) at the small distal cross-section is 2.5-40% less than the small finger sleeve width (630) at the small proximal cross-section, and (b) a first small finger sleeve circumference at the small distal cross-section is 2.5-40% less than a second small finger sleeve circumference at the small proximal cross-section.

19. The glove (100) of claim 18, wherein the small finger sleeve aperture length (681) is no more than three times the small finger sleeve aperture leading edge offset (684), and the small finger sleeve aperture open area does not exceed 20% of the small finger sleeve total surface area, and the thumb sleeve aperture open area does not exceed 20% of the thumb sleeve total surface area.

20. The glove (100) of claim 18, wherein an average small finger aperture zone circumference of seven small finger cross-sections within a small finger aperture zone are centered about a small finger aperture centroid cross-section and spaced 5 mm apart, is less than 5.4 cm, and an average small finger non-aperture zone circumference is 2.5-20% greater than the average small finger aperture zone circumference.

* * * * *